United States Patent [19]
Scott et al.

[11] Patent Number: 5,723,754
[45] Date of Patent: Mar. 3, 1998

[54] TAPETUM-SPECIFIC PROMOTERS FROM BRASSICACEAE SPP

[76] Inventors: Roderick John Scott, 95 Martopp Road, Clarendon Pk, Leicester LE2 1 WG; John Draper, 10 Shirley Road, Stoneygate, Leicester LE2 2 LJ; Wyatt Paul, Flat 5, 74 Stoughton Rd., Leicester LE2 2EB, all of Great Britain

[21] Appl. No.: 417,460

[22] Filed: Apr. 5, 1995

Related U.S. Application Data

[63] Continuation of Ser. No. 78,228, filed as PCT/GB91/02317, Dec. 24, 1991 published as WO92/11379, Jul. 9, 1992, abandoned.

[30] Foreign Application Priority Data

Dec. 24, 1990 [GB] United Kingdom ................ 9028060

[51] Int. Cl.$^6$ .............................. A01H 5/00; C12N 15/12; C12N 15/82
[52] U.S. Cl. .................. 800/205; 536/23.6; 536/24.1; 435/69.1; 435/172.3; 435/240.4; 435/252.3; 435/320.1
[58] Field of Search ................................... 800/205, 250; 536/24.1, 23.6; 435/69.1, 172.3, 240.4, 252.3, 320.1

[56] References Cited

FOREIGN PATENT DOCUMENTS 344029 11/1989 European Pat. Off. .
90 08828 8/1990 WIPO .

OTHER PUBLICATIONS

Scott, R., et al.; "Identification of Genes Exhibiting *Brassica napus*;" Journal of Experimental Botany; vol. 41, 1990, Suppl., P5-3.

Hodge, R. P., et al.; "A9 a Tapetum–Specific Gene;" Journal Experimental Botany; vol. 42, 1991, 238 Suppl.; Meeting Apr. 7–12; 1991; p. 46.

Paul, W. et al.; "Aspects of the Molecular Biology of Anther Development"; Journal Experimental Botany; vol. 42, 1991, 238 Suppl.; Meeting Apr. 7–12; 1991; p. 40.

Roberts, M., et al.; "Isolation and Characterization of Pollen Specific Promoters from *Arabidopsis thaliana*"; Journal Experimental Botany; vol. 41, 1990, Suppl., P5-2.

Mariani, C., et al.; "Induction of Male Sterility in Plants by a Chimaeric Ribonuclease Gene;" Nature; vol. 347; 25 Oct. 1990; pp. 737–741.

Barghchi, M. et al.; "Genetic Engineering of Arabidopsis;" Abstracts VIIth International Congress on Plant Tissue and Cell Culture; 1990, Jun. 24–29, Amsterdam, NL; p. 46.

Kim et al. (1994) Plant Mol Biol 24:105–117.

*Primary Examiner*—Elizabeth McElwain
*Attorney, Agent, or Firm*—Hale and Dorr

[57] ABSTRACT

Tapetum-specific promoters, designated A3 and A9 and capable of driving expression of 12.9 kDa and 11.6 kDa proteins in *Arabidopsis thaliana* and related proteins within the family *Brassicaceae*, have been discovered, isolated and cloned. The promoters can be used to drive male sterility DNA such as that coding for a nuclease, protease or glucanase. Alternatively or in addition, male sterility can be achieved by disrupting the proper expression of the A3 and/or A9 genes, for example by transcribing RNA which is antisense to the RNA normally transcribed from the A3 and A9 genes, or by expressing DNA coding for a ribozyme specific for at least one of the A3 and A9 genes.

28 Claims, 34 Drawing Sheets

DNA sequence of the B. napus cDNA clone A3.

```
    S   S   F   C   L   L   L   L   V   V   F   E   L   N   S   Q   P   A   L
TTTCTTCTTTCTGTTACTCCTCCCTCGTCGTCTTCTTCCTCAATTCTCAACCTGCACTCT
         10        20        30        40        50        60

S   L   R   V   P   K   P   Q   S   E   P   A   S   P   Q   T   M   I   D   D
CACTCCGTGTCCCAAAACCGCAGTCAGAACCAGCATCACCACAAACCATGATCGATGACT
         70        80        90       100       110       120

S   S   P   M   G   M   I   D   H   A   K   S   M   I   A   G   F   F   S   H
CATCTCCAATGGGAATGATCGACCATGCAAAGTCCATGATTGCTGGATTCTTCAGCCACA
        130       140       150       160       170       180
```

FIG.1(a)

```
K  F  P  V  M  G  W  P  F  P  K  Y  P  P  F  T  M  V  N  P
AGTTCCAGTAATGGGCTGGCCCTTCCCCAAGTACCCCACCTTTCACAATGGTCAACCCTA
         190          200          210          220          230          240

N  V  P  T  N  P  S  G  A  Q  E  E  S  E  K  L  P  S  S  P
ACGTTCCAACAACCCATCTGGAGCTCAAGAGGAATCAGAGAAGAAGCTACCTTCTTCCCCAA
         250          260          270          280          290          300

S  K  L  N  K  A  G  R  N  A  *
GCAAACTTAACAAAGCTGGACGAAAACGCATGAAAAATTGTTGTTGGAA
         310          320          330          340
```

FIG. 1(b)

Homology between the DNA sequences of the B. napus E5 and E3 cDNA clones and the A. thaliana A3 gene.

```
Percent Similarity:  81.7 -- At A3 vs Bn E5
                     80.0 -- At A3 vs Bn E3
                     95.2 -- Bn E5 vs Bn E3
```

```
770 ATGTCGAAAATCTCAAAAGCTTCTTCTCTCTGTTTACTCCTTCTCTGTCTT 819  At A3
    ||| | ||||||| ||| ||| ||| ||||||||||||||||| |||||
1   ............AAAGGTTTCTTCTTTCTGTTTACTCCCTCCTGTCGT  36  Bn E5
                                |||||| |||||||||||||
1   .........................GCCCCTCCTGTCGT  17  Bn E3

820 CTTCCTCTTCAGTTCCCGGACCCGCACTCTCACTCCGTGGCCCAAAACTTC 869  At A3
    ||| || ||| || || ||  |||||||||||||||||| |||||||| |
37  CTTCTTCCTCAATTCTCAACCTGCACTCTCACTCCGTCCCAAAACCGC  86  Bn E5
    ||||||||||||||||||||||||||||||||||||||||||| |||||
18  CTTCTTCCTCAGTTCTCAACCTGCACTCTCACTCCGTCTCCCAAAACCGC  67  Bn E3
```

FIG. 2(a)

```
870  AATCATCGGAACCAAAATCAGCTCAAACCCTAATGGATGATTCGTCTTCA   919
      |||   |||||  |||||   ||||  |  |||| |||| |   ||  || ||
 87  AGTCA...GAACCAGCATCCACCACCAAACCATGATCGATGACTCATCTCCA   133
      |||||    ||||   |||||||||||| |||||||||||||| ||||||
 68  AGTCA...GAACTAGCATCACCCTCAAACCATGATCGATGACTCATCTCCA   114

920  ATGAACAAGATCAACTCTGGAAATGCAAA.......CATGATTGCTGGTTTCTT   969
      |||    ||||   ||     ||||||||        ||||||||||| |||||
134  ATGGGAATGATCGAC.......CATGCAAAGTCCATGATTGCTGGATTCTT   177
      |||||||||||||||        |||||||||   |||||||||||||||||
115  ATGGGAATGATCGAC.......CATGCAAAGCCATGATTGCTGGATTCTT   158

970  CAGTCACAAGTTTCCATTAAAGGGCTGGCCTTTCCCTAAGTACCCACCTT   1019
      |||  ||||||||||| |||| ||||||||||||||| ||||||| ||||
178  CAGCCACAAGTTTCCAGTAATGGGCTGGCCTTTCCCCAAGTACCACCTT   227
      |||||||||||||||| |||||||||||||||||||  |||||||| |||
159  CAGCCACAAGTTTCCACTAATGGGCTGGCCTTTCCCAAAGTACCCACCCT   208
```

FIG. 2(b)

```
1020  TCCCTATGGTTAACCCTAATATTGCAACAAACCCATCTGGAGCTCAAGAG  1069
      ||  ||||  |||||  ||  ||||||| ||||||||||||||||||||
 228  TCACAATGGTCAACCCTAACGTTCCAACAAACCCATCTGGAGCTCAAGAG  277
      ||||||||||||||||||||||||||||||||||||||||||||||||||
 209  TCACAATGGTTAACCCTAACGTTCCAACAAAACCATCTGGAGCTCAAGAG  258

1070  GAATCCGCAAAGTTACCTTCTCTCCAAGCAAAACTTAACAAAGATGGACG  1119
      |||| | ||||||||||||| ||||||||||||||||||||||||||||
 278  GAATCAGAGAAGCTACCTTCTCCCCAAGCAAAACTTAACAAAGCTGGACG  327
      |||||||||||||||||||||||||||||||||||||||||||||||||
 259  GAATCAGAGAAGTTACCTTCTTCCCCAAGCAAAACTTAACAAAGATGGACG  308
```

FIG.2(c)

```
1120 AAACGCTTGAAGATTAGAGTT.TACTTATTTATATGGTTT.....TTACCA 1169
      ||||| |||| ||   |||  |||   ||||   ||| ||||||  |||||
 328 AAACGCATGAAAATTGTTGTTGGAAACATTTCTATGGTTTTACATTTTCA 377
     |||||||||||||||||||||||||||||||||||||||||||||||||
 309 AAACGCATGAAAATTGCTGTTGGAAACATTTCTATGGTTTTACATTTTCA 358

1170 TTGCATCAAATAAAAAAATGTACCTTTAACAATTAAATGGTAAAAGAAAAA 1219
       ||  |||  ||| ||||||   |||||||||| |||||||| ||
 378 TTAAAATAAAAATAAAATTGTATCTTTAACAATTGAATGGTAAGCG..... 422
     ||||||||||
 359 TTAAAATAAAG..AAATTGTATCTTTAACAATTGAATGGTAA........ 398
```

FIG.2(d)

Alignment of the putative polypeptides encoded by B.napus E5 and E3 cDNAs and the A.thaliana A3 gene.

```
*  :=>  match across all seqs.
.  :=>  conservative substitutions

At A3   MSKISKASSLCLLLVFFLFSSRPALSLRGPKLQSSEPKSAQTLMDDSSSMNKINSGNAK
Bn E5   -----KVSSFCLLLVVFFLNSQPALSLRVPKPQS-EPASPQTMIDDSSPMGMID--HAK
Bn E3   ---------ALLVVVFFLSSQPALSLRLPKPQS-ELASPQTMIDDSSPMGMID--HAK
               **  ....*.******* ** **** *  .******.*..*. .**

At A3   TMIAGFFSHKFPLKGWPFPKYPPFPMVNPNIATNPSGAQEESAKLPSSPSKDNKDGRNA
Bn E5   SMIAGFFSHKFPVMGWPFPKYPPFTMVNPNVPTNPSGAQEESEKLPSSPSKLNKAGRNA
Bn E3   AMIAGFFSHKFPLMGWPFPKYPPFTMVNPNVPTKPSGAQEESEKLPSSPSKLNKDGRNA
         **********.. ********** ******. *.********.*********.**.****
```

FIG.2(e)

DNA sequences of the A. thaliana A3 gene.

```
GTCGACACTATTTGTTAATCAGTAGACTTCATTGTGCTGCCTTTGGCTTCTTTTCGTCGG
         10        20        30        40        50        60

AAAAACAGCTGAATGTGACTCTAATTTCGGGCAGCAAACGCGGGCCGTTCATGGCCGG
         70        80        90       100       110       120

AGGTAGGAAAGAACGGGAACAAAACACGCCGAGATGGGACAAAATCTGTGACAGATTCGCCA
        130       140       150       160       170       180

CTTACTGTGATCACGGGCCGCCGGGAGCATTAATCGCCGCATTCGCCGGCGTAATCCTTATGC
        190       200       210       220       230       240
```

FIG. 4(a)

```
TCATCATCTCCGCCGGTCAATCTCTCGTCCAACCTAATAAATGCTGCTCCACCA
         250       260       270       280       290       300

CCGCATCTCCCCTCGGTCGTCCCCTGAAAACATACACACGTGTCACGTTCCCCCTGTTATTT
         310       320       330       340       350       360

TCCTTTTCTTTTTCTTACTTCTTTGTTTCTTCTTGAGTGTGGTGTATCTCGAGTGAA
         370       380       390       400       410       420

TGTGATTGATCAGATTGTGTAAGCATTTGGCTCGTCTCTTCTTTGTAAAACTTTCTTCTT
         430       440       450       460       470       480
```

FIG. 4(b)

```
ATGGTTTATTCTTAAACCTAATTCTCCGACTAGGGTTAGGTTACTAAAATATCCATTACCT
        490           500           510           520           530           540

ATACTCGTTATCAATACCCATACTCGTTATATCAACCATAAATCATCTCTCATAGTCATG
        550           560           570           580           590           600

CTCAAATCATGAACCTTTTTAATTCGAATACTGGTTTAGGTAAGAAGTAGAATCCCAACG
        610           620           630           640           650           660

TAAAAAACACATCTCTTCTACAAACTCAAAAATCACTACTATATAAGATTACCAAGAAAC
        670           680           690           700           710           720
```

```
                                                          M   S   K   I
CCCATAAAACACAATCACAAGAGAGCTCAAAAACACCAAGCAAAATGTCGAAAAT
         730           740           750           760           770           780

S   K   A   S   S   L   C   L   L   L   L   V   F   F   L   F   S   S   R   P
CTCAAAAGCTTCTTCTCTGTTACTCCTTCTTCTCTTCCTCTCTTCAGTTCCCGACC
         790           800           810           820           830           840

A   L   S   L   R   G   P   K   L   Q   S   S   E   P   K   S   A   Q   T   L
CGGCACTCTCACTCCGGTGGGCCCAAAACTTCAATCATCGGAACCAAATCAGTCAAACCCT
         850           860           870           880           890           900

M   D   D   S   S   S   M   N   K   I   N   S   G   N   A   K   T   M   I   A
AATGGATGATTCGTCTTCAATGAACAAGATCAACTCTGGAAATGCAAAACCATGATTGC
         910           920           930           940           950           960

G   F   F   S   H   K   F   P   L   K   G   W   P   F   P   K   Y   P   P   F
TGGTTTCTTCAGTCACAAGTTTCCATTAAAGGGGCTGGCCCTTTCCCCTAAGTACCCACCTTT
         970           980           990           1000          1010          1020
```

```
  P   M   V   N   P   N   I   A   T   N   P   S   G   A   Q   E   E   S   A   K
CCCTATGGTTAACCCTAATATTGCAACAAACCCATCTGGAGCTCAAGAGGAATCCGCAAA
         1030              1040              1050              1060              1070              1080

L   P   S   S   P   S   K   D   N   K   D   G   R   N   A   *
GTTACCTTCTCTCCAAGCAAAGACAACAAAGATGGACGAAACGCTTGAAGATTAGAGTT
         1090              1100              1110              1120              1130              1140

TACTTATTTATATGGTTTTTACCATTGCATCAAATAAAAAATGTACCTTTAACAATTAAA
         1150              1160              1170              1180              1190              1200

TGGTAAAAGAGAAAAAAGATATTTATATATCATCAGCTCGAAGCGATTTGTTATGACAGTT
         1210              1220              1230              1240              1250              1260

ACAGGAATATTAACAA
         1270
```

FIG. 4(e)

DNA sequence of the B. napus cDNA clone A9.

```
                   M  E  F  L  K  S  F  T  T  I  L  F  V  M  F  L  A
TAAACAAAAATGGAATTTCTCAAATCCTTTACAACTATTCTCTTTGTAATGTTTCTGGCCA
         10        20        30        40        50        60

M  S  A  L  E  T  V  P  M  V  R  A  Q  Q  C  L  D  N  L  S
TGAGCGGCTCTGGAGACCGTACCTATGGTTCGAGCTCAACAATGCCTAGACAATTTGAGCA
         70        80        90       100       110       120

N  M  Q  V  C  A  P  L  V  L  P  G  A  V  N  P  A  P  N  S
ATATGCAGGTGTGTGCCCCGCTCGTGCTGCCTGGTGCAGTCAATCCAGCCCCGAATTCAA
        130       140       150       160       170       180

N  C  C  I  A  L  Q  A  T  N  K  D  C  I  C  N  A  L  R  A
ATTGCTGCATTGCTCTCCAAGCAACTAACAAAGATTGTATATGTAACGCCCTTCGAGCAG
        190       200       210       220       230       240
```

FIG. 5(a)

```
  A  T  T  F  T  T  T  C  N  L  P  S  L  D  C  G  I  T  I  *
CCACCACATTACCACTACTGCAACCTCCCCTCTTTAGATTGTGGTATAACCATATGAG
         250          260          270          280          290          300

TGGTTTCAGCAACGGTCAGTTCCGAGGATTTGGGGAGTTTGGTCTGCAAAAGACAACAAG
         310          320          330          340          350          360

AATAAAGTATTAAAAATAACGAGAAAGTGTGTGTTTTTTTAATTGGTCTCTGTTGTT
         370          380          390          400          410          420

CGGTTGGTTCAATACTTAAAATATGACCCATCAATTAATATCGTTTTCATATTTATTATGG
         430          440          450          460          470          480

TAATATTTTT
         490
```

FIG. 5(b)

DNA sequences of the A.thaliana A9 gene.

TCTAGACATAACGGTGAGAGTTAATATTAAAATTTCAGGCGAGAAAAATGATACTTGAAA
         10        20        30        40        50        60

AATATTATGATCGTTTTGGATATTCCTTACATCGAGTGAATGTTGGTTTGATTCATCTTC
         70        80        90       100       110       120

CAAGTGTTCTGCAAACGTATATTAAAGGTTTATTAACTGGTAAGAGATTAACCGGGTTTT
        130       140       150       160       170       180

GGTTCAGCATATACCATGATTGACTAACTGATCAAATAGTCTTTACTTATTATATAAAGA
        190       200       210       220       230       240

CGATACTATTGGTCATGCTACAAAATCAAGTCATACCATATCCCTGAGAATGAATGTGGAG
        250       260       270       280       290       300

FIG.7(a)

```
AATCGTTATAAGGCATAAGTGTGGGTATTGATCGTGGTACGAACAACCGCCTTGGCATCA
         310       320       330       340       350       360
ACATTAGCCACGATATCCAACATTTGAAGCATTGCCTATGGGCGAGTGTTTGGTTTGGTTTT
         370       380       390       400       410       420
GAAACTGATGATGATAACCAGAACGAGAAATGTCTTGTGAAGTATAAATGTTCCGATGAAT
         430       440       450       460       470       480
TGGGATTATAATAATGTGTAGACATTGTAGGTTGGTTTTGATGATGATAAGTAATCATTG
         490       500       510       520       530       540
GAGAATTGTCTAACACATGCACTGGGAGAATTATTGACTCTACCACGTTCTCTCTTTGATATT
         550       560       570       580       590       600
```

```
CCTCGATTTCCCTCGTGATTTCATCAGCCCTCTCCGAAAAAGTAATTGTATCCACTAGAAC
         610       620       630       640       650       660

TTTGGGAATCTCCCATCTAATTTATGTATTAGAGAAGTTATAATATTTTGGGGAAATAGA
         670       680       690       700       710       720

TTTCTCTACTGATTTGTTGTGTGACATTATATTTTATAAGTACATGTTTCTGTTTCG
         730       740       750       760       770       780

TTATATTGTGTTGTCGTGGTTGAGTCTTTATTAGAGCATGTAAATATGTTTATGAAATAAGC
         790       800       810       820       830       840

GAGAAAGGAATTAATTAAACGTATCGAGTGATAAATGCTTTAATGGATTCGAGATTTAGT
         850       860       870       880       890       900
```

```
ATTCTTAAATTTTGTTTCATTATCATTGATTATAAACTAAGTTATGTTGATCTCAAAT
        910       920       930       940       950       960

CCTTAATTATGTTCTCCCTAAGAAGAGTAGTACAAGTGGTGGGAACGAAAGATGAGTAAAATAC
        970       980       990      1000      1010      1020

TAAAAATCTTTTCTCAAAAGTCAAATCGCATTAGTTAACAAAAAACAAACCATGTGTTACC
       1030      1040      1050      1060      1070      1080

GTCAAATCAATGTGTTTAAAAGATGTTAACCACTAATCAAGCATTTACGTGTAACCGGAT
       1090      1100      1110      1120      1130      1140

CAACCGGATTTGGGTTTTGAATATGTTGTGTGGAGAGTGTATATAAATGATAAATTAATTGAA
       1150      1160      1170      1180      1190      1200
```

FIG.7(d)

TATCTTAATTAATCTGTGAAAGAAACTACATCACACACTTTGTTATTCCCCTAGCTTTT
1210      1220      1230      1240      1250      1260

AGTTTTTTATCATGCAAAACTTATGAAGTAACTAGATCAAGATCACAAAAAAAAGCAT
1270      1280      1290      1300      1310      1320

CACTTCACTTCATGACCTAATTATTCTCGAAGCCCAAAACTATTTACATACACTTTTATT
1330      1340      1350      1360      1370      1380

CTATAAATATAGATGATGGAATTCACCAATCCAAAAGTGAATAAAAAACACAAGTACAAA
1390      1400      1410      1420      1430      1440

M  V  S  L  K  S  L  A  A  I  L  V  A
CAATATAGTATCTAATTAGAATGGTATCTCTAAAGTCCCCTTGCTATTCTCGTTGCCA
1450      1460      1470      1480      1490      1500

```
  M  F  L  A  T  G  P  T  V  L  A  Q  Q  C  R  D  E  L  S  N
TGTTTCTTGCCACCGGACCTACGGTTCTAGCCCAGTGCAGAGACGAACTGAGCAATG
         1510           1520          1530          1540          1550          1560

V  Q  V  C  A  P  L  L  L  P  G  A  V  N  P  A  A  N  S  N
TGCAGGTGTGCGCGCCGCTGCTTCTGCCCGGTGCGGTCAATCCTGCCGCGAACTCAAATT
         1570          1580          1590          1600          1610          1620

C  C  A  A  L  Q  A  T  N  K  D  C  L  C  N  R  L  R  A  A
GCTGCGCTGCCCTCCAAGCAACTAACAAAGATTGTCTATGTAACCGTCTTCGAGCAGCCA
         1630          1640          1650          1660          1670          1680

T  T  L  T  S  L  C  N  L  P  S  F  D  C  G  K  M  I  H  R
CCACACTTACCCTCTCTTTGTAACCCTCCCCTCTTTTGATTGTGGTAAGATGATCCATCGAT
         1690          1700          1710          1720          1730          1740

L  K  P  F  L  L  D  F  Y  K  L  F  H  Q  *
TAAAACCTTTTTTACTAGATTTTATAAATTATTCCATCAATAGTGTTTGTTTTATATTT
         1750          1760          1770          1780          1790          1800
```

```
GTTCTCATGATTTTTGGACTTATGTGTTTTGTGAACTGTGCAGGCATAAGTGCCTAGTTGA
          1810      1820      1830      1840      1850      1860
ACAACATTCAGTTCCGAGGATTTGGGGAGTTTGGTCTGCAAACGACAAGACGAATAAAAT
          1870      1880      1890      1900      1910      1920
AAAATAATGAGAAAATACACTATTTAGTGTTTT
          1930      1940      1950
```

FIG. 7(g)

DNA homology between the B. napus A9 cDNA and the
A. thaliana A9 gene.

```
                                                            Bn A9    At A9
   1 TAAACAAAAATGGAATTTCTCAAATCCTTTACAACTATTCTCTTTGTAATG    50
     ||| | ||||| || || ||| ||| || ||||||| || ||||||||||
1453 TAATTAGAATGGTATCTCTAAAGTCCCCTGCTATTCTCGTTGCCATG        1502

51 TTTCTGGCCATGAGCGCTCTGGAGACCGTACCTATGGTTCGAGCTCAACA    100
     ||||| ||| |||||||| |||| ||| || ||| || || || || ||
1503 ...........ACCGGACCTACGGTTCTAGCCCCAGCA                 1537

101 ATGCCTAGACAATTTGAGCAATATGCAGGTGTGCGGCCGCTGGTTCTGC     150
     ||| |||| |||||||||| ||||| |||||||| ||||| |||||||||
1538 GTGCAGAGACGAACTGAGCAATGTGCAGGTGTGCGGCCGCTGCTTCTGC     1587
```

FIG. 8(a)

```
 151 CTGGTGCAGTCAATCCAGCCCGAATTCAAATTGCTGCATTGCTCTCCAA  200
     |||||  ||||||||||  |||  ||||   ||||||||||||  |||  ||||||
1588 CCGGTGCGGTCAATCCTGCCGCGAACTCAAATTGCTGCGCTGCCCTCCAA 1637

201 GCAACTAACAAAGATTGTATATGTAACGCCCTTCGAGCAGCCACCACATT  250
     ||||||||||||||||||  ||  ||||| ||||||||||||||||||| -
1638 GCAACTAACAAAGATTGTCTATGTAACCGTCTTCGAGCAGCCACCACACT 1687

251 TACCACTACTTGCAACCCTCTCTTTAGATTGTGGTATAACCAT......  295
     ||||  ||  ||||| |||||||||||| ||||||||||||||  ||
1688 TACCTCTCTTTGTAACCCTCCTCTTTGATTGTGGTAAGATGATCCATC  1737

296 .......ATGAGTGGTTTCAGCAACGGTCAGTTCCGAGGATTGGGGAGT  338
            ||  ||  ||   |   ||    ||      |||     ||
1738 GATTAAACCTTTTTTACTAGATTTTTATAAATTATTCCATCAATAGTGT 1787
```

FIG. 8(b)

```
 339 TTGGTCTGCAAAAGACAAGAATAAAGTATTAAATAACGAGAAAGT  388
     ||| | ||  |   |  || ||  |   | ||  |   |   |||
1788 TTGTTTTATATTGTTCTCATGATTTTTGGACTTATGTTTTGTGAACTG 1837

389 GTGTGTGTTTTTTTTAATTTGGTCTCGTGTTGGTTCAATACTTA  438
     | | ||| |             |  |   |  | |||  |    |
1838 TGCAGGCATAAGTGCCTAGTTGAACAACATTCAGTTCCGAGGATTTGGGG 1887

439 AATATGACCCATCAATTAATATCGTTTCATATTTATGGTAATATTT  488
     | | |   | ||  ||   || ||  |   |  ||   | ||  |
1888 AGTTTGGTCTGCAAACGACAAGACGAATAAAATAAATAATGAGAAATAC 1937

Alignment of the putative polypeptides encoded by
B.napus A9 cDNA and the A.thaliana A9 gene Percent Similarity: 72.8

```
Bn A9   1 MVSLKSLAAILVAMFLA......TGPTVLAQQCRDELSNVQVCAPLLLPGA  45
          ||| ||| ||||  ||||        || |||||||  ||||||| |||||
At A9   1 MEFLKSFTTILFVMFLAMSALETVPMVRAQQCLDNLSNMQVCAPLVLPGA  50

Bn A9  46 VNPAANSNCCAALQATNKDCLCNRLRAATTLTSLCNLPSFDCGKMIHRLK  95
          ||||| ||||| ||||||||| || |||| ||| |||||  ||| |  |
At A9  51 VNPAPNSNCCIALQATNKDCICNALRAATTFTTTCNLPSLDCGITI...  97

Bn A9  96 LFHQ  99
```

FIG. 8(d)

pWP78

3.8 kb Ap$^R$
pBluescript
derivative pWP80

3.8 kb Ap$^R$
pJIT60
derivative pWP88

3.6 kb Ap$^R$
pJIT60
derivative 1 kb

Key to DNA sequences  ☐ promoter   ■ polyA signal

Key to DNA sequences

▓ Barnase

▨ Barstar

☐ Tapetum-specific promoter

■ CaMV polyadenylation signal

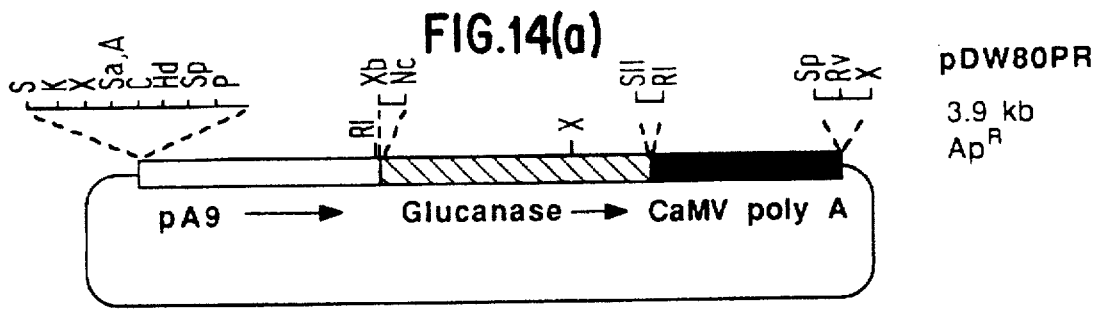
FIG.14(a) pDW80PR 3.9 kb Ap^R
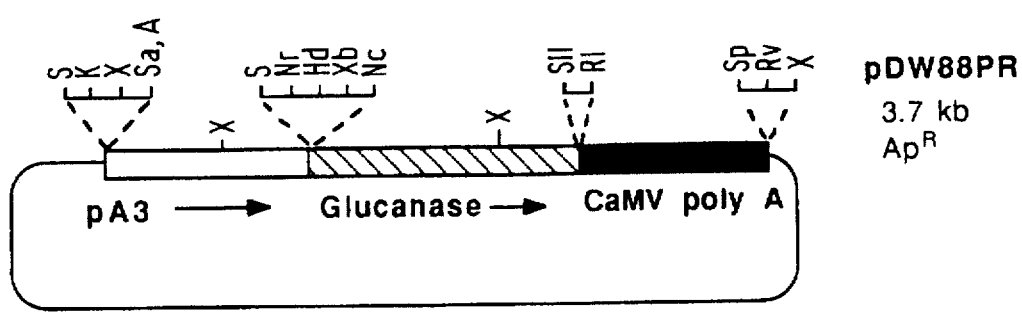
pDW88PR 3.7 kb Ap^R
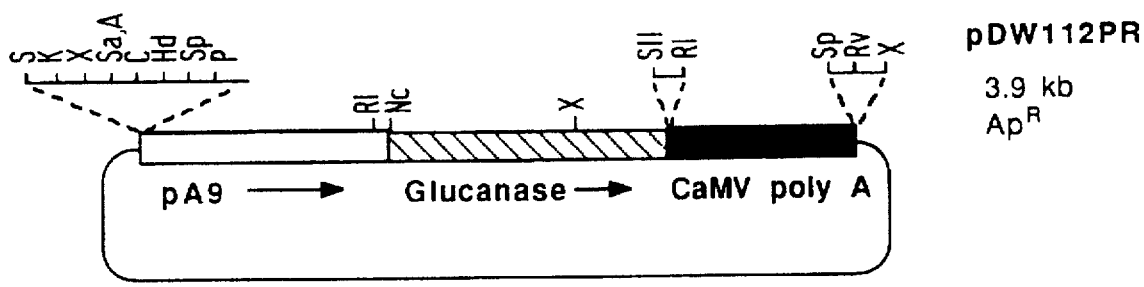
FIG.14(b) pDW112PR 3.9 kb Ap^R
1 kb
Key to DNA sequences
▨ Coding
☐ Promoter region
■ PolyA signal

TAPETUM-SPECIFIC PROMOTERS FROM BRASSICACEAE SPP

This application is a continuation of application Ser. No. 08/078,228, filed as PCT/GB91/02317, Dec. 24, 1991 published as WO92/11379, Jul. 9, 1992, now abandoned.

BACKGROUND OF THE INVENTION

This invention relates to the application of recombinant DNA technology to plants, specifically for the purpose of achieving male sterility.

The production of hybrids via sexual hybridisation of parents with differing genetic backgrounds is an important practice in modern agriculture. Due to the manifestation of heterosis or hybrid vigour the offspring are superior to the parents in such key agronomic characters as yield and disease resistance. Further, where the parents are extensively homozygous, the resulting offspring are genetically very uniform and therefore the crop behaves in an equally uniform manner in such important characteristics as germination time, height of growth, susceptibility to disease, flowering time, seed ripening time etc, which greatly improves the efficiency of crop management. For these reasons hybrid seed is attractive to the farmer and therefore sells at a premium.

In nature, the reproductive organs of many plant species are arranged in a manner that greatly favours self-fertilisation and consequently the production of non-hybrid offspring. Therefore, in order to produce hybrid seed free from contamination with selfed seed, cross-fertilisation is carried out using a variety of mechanical, chemical and genetic methods that prevent self-pollination.

An important mechanical method for hybrid seed production is available for *Zea mays*. In this species, the male and female reproductive organs are located on different parts of the same plant, which facilitates emasculation by a process known as detasseling—removal of the anthers. However, the reproductive organs of most other major crops are not so conveniently arranged making emasculation a very labour-intensive operation; as a consequence, hybrid seed produced by this method is very expensive.

Chemical methods rely on gametocide, such as etherel, which kill or block viable pollen production. However, such chemicals are usually expensive and difficult to administer, particularly to crops with an indeterminate flowering habit.

Two commonly used genetic methods for preventing self-pollination are self-incompatibility and male sterility. In self-incompatibility systems, viable pollen is produced but a biochemical block prevents self-pollination by interfering with pollen germination or pollen tube growth. However, such systems are complicated by the scarcity of self-incompatible female lines, propagation difficulties and the frequent instability of the self-incompatibility. In some cases, the problems of propagation can be eased by chemical suppression of the self-incompatibility or by the hand pollination of immature buds ("bud pollination") before activation of the biochemical block to self-pollination. However, suppressible self-incompatibilities are often vulnerable to climatic stress which reduces the effectiveness of the system. The important crop genus *Brassica* provides a good example of the difficulties associated with self-incompatibility systems for hybrid seed production. Although self-incompatibility is widespread in *Brassica* spp., the system is complex, female lines are very difficult to propagate and the self-incompatibility is prone to breakdown under stressful climatic conditions.

In agricultural terms, the most important natural mechanism employed to prevent self-pollination is so-called male sterility. Male sterility usually results from the manifestation of certain mutations carried in the nuclear or organellar (chloroplastic and mitochondrial) genomes that result in the degeneration of the anthers or pollen prior to dehiscence (release of pollen). Plants expressing male sterility are therefore female only, and any seed produced by such plants must be the product of cross-pollination from a male fertile plant. Currently, the greatest barrier to the widespread availability of hybrid seed is the absence of effective male-sterility.

Naturally occurring male sterility systems are available in several crops: maize, sugarbeet, oilseed rape and sunflower. Many have flaws such as the breakdown of sterility and the production of pollen under stressful climatic conditions. Genetically controlled male sterility has previously relied mostly upon the chance discovery of male sterile plants in the breeding population. The development of an effective male sterility system would remove this dependence on an unpredictable event and give more control to the plant breeder. The present invention relates to such a development.

The promoter is that region of a gene which regulates its expression, for example by specifying the time or location of expression. Promoters can be separated from the coding region of a gene and used to drive a different coding region, thus allowing the expression of a different product. A promoter can in principle be used to effect male sterility if it is specific to the cells/tissue involved in the production of male gametes. The tapetum is a specialised cell layer within the anther that plays a crucial role in the supply of nutrients to the developing microspores. Malfunction of the tapetum is the cause of many types of natural male sterility.

According to EP-A-0329308 (Paladin Hybrids Inc), many of the difficulties associated with naturally-based male-sterility and sexual incompatibility systems can be overcome by a proposed "artificial" male-sterility system. EP-A-0329308 describes several possible variants of the system. In one type, the central element is a chimeric gene consisting of a microspore-specific promoter and a male sterility DNA. Microspores are immature pollen grains. The important property of male-sterility DNA is that its expression is designed to cause the termination of microspore development, by interfering with processes unique or essential to it. Since the promoter is microspore-specific, the male-sterility DNA is transcribed into RNA only in the microspores. The application describes several types of male-sterility DNA, specifying: anti-sense RNA to microspore-specific genes and to proteins with a general, but essential, cell function (eg actinidin and tubulin); and the cytotoxic proteins Ricin A and diphtheria toxin.

However, the system as described appears to have a serious drawback, in that the teaching of EP-A-0329308 would not produce plants which are necessarily male-sterile plants. Since the action of the microspore-specific promoter described in the invention occurs post-meiosis, segregation of the male sterility DNA in the microsporocytes of plants heterozygous for the factor would result in only half the pollen grains receiving the factor.

A possible way to circumvent the segregation problem would be to generate plants homozygous for the sterility factor. However, propagation of such a plant would have to proceed via asexual processes since any pollination would again return the offspring to heterozygosity. This limits the application of the invention to plant species where such propagation is commercially viable. It would therefore be desirable for male sterility DNA to be expressed in the mother tissue thereby to affect all the pollen grains.

EP-A-0344029 (Plant Genetic Systems (PGS)) also describes an artificial male sterility system for use in hybrid seed production. It is based on a chimeric gene consisting of an anther-specific promoter (from the gene designated TA29) isolated from *Nicotiana tabacum* and a male sterility DNA. In this case, the promoters are derived not from microspore-specific genes as in the Paladin system, but from genes expressed exclusively within the tapetum. Hence, the chimeric gene is designed to prevent microspore development and cause male-sterility by disrupting or destroying the tapetum.

The most important difference between this approach and that of EP-A-0329308, is that the choice of a promoter which is active in a cell-type not subject to meiosis, avoids the problems associated with genetic segregation. Destruction of the tapetum prevents the maturation of all microspores regardless of genetic make-up.

As part of the continuing endeavour to improve the means available to the plant geneticist for inducing male sterility in commercially important crops and other plants, the identification of further useful genes and associated promoters is actively sought. Among the commercially most significant crops in the world today are included members of the family Brassicaceae, particularly *Brassica napus*, commonly known as oil-seed rape. If tapetum-specific genes and promoters from members of the family Brassicaceae could be elucidated, plant breeders would have at their disposal powerful tools to use in the development of male sterile *B. napus* and other members of the Brassicaceae family. There is an attraction in being able to keep heterologous DNA within the family or smaller taxonomic division, as unpredicted effects may be reduced or minimised. Further, transgenic members of the family Brassicaceae incorporating heterologous DNA from other members of the same family may well be more acceptable from the regulatory point of view than Brassicaceae family members incorporating DNA from more remote sources.

SUMMARY OF THE INVENTION

The present invention is based on the discovery of novel and useful genes and promoters from the family Brassicaceae and relates to methods, genetic constructs and transgenic plants harnessing the discovery.

According to a first aspect of the present invention, there is provided a recombinant or isolated DNA molecule comprising a promoter which naturally drives expression of a gene encoding an 11.6 or 12.9 kDa tapetum protein in *Arabidopsis thaliana* or an equivalent protein in another member of the family Brassicaceae.

In this specification, the gene encoding the 12.9 kDa protein in *A. thaliana* and equivalents of that gene in other members of the family Brassicaceae will be referred to as the A3 gene; the gene encoding the 11.6 kDa protein in *A. thaliana* and equivalents of that gene in other members of the family Brassicaceae will be referred to as the A9 gene. The A9 and A3 are different in sequence and pattern of expression from the tapetum-specific promoters described in EP-A-0344029. Induction by external factors such as heat shock or herbicide application, as is described in one embodiment of EP-A-0329308, is not required for this invention to function, so it need have none of the attendant problems with, for example, indeterminate flowering habits.

A3 temporal expression spans the period in anther development when the microsporocytes are in meiotic division to early microspore interphase. A9 gene is expressed in tapetal cells. Expression of A9 is initiated in anthers that contain meiocytes and continues into anthers that contain microspores in early first interphase.

The molecular weights quoted above are putative and derived from the number of amino acids believed to be present, as deduced from the DNA sequence. The 12.9 kDa protein encoded by the A3 gene of *A. thaliana* has 118 amino acids; the 11.6 kDa protein encoded by the A9 gene of *A. thaliana* has 107 amino acids. It will therefore be appreciated that the molecular weights refer to the un-glycosylated protein. In addition, the effect on any other post-translational processing such as partial proteolysis is discounted.

Although figures given above relate only to proteins of *A. thaliana*, those skilled in the art will readily be able to identify equivalent proteins from other members of the family Brassicaceae. For example, the equivalent A9 gene in *Brassica napus* encodes a putative protein of 96 amino acids in length having a calculated molecular weight of 10.3 kDa. Such equivalent genes may be identified by hybridisation studies, restriction fragment length polymorphism (RFLP) and other methods known in the art. Genes encoding closely equivalent proteins may for example hybridise under stringent conditions (such as at approximately 35° C. to 65° C. in a salt solution of approximately 0.9 molar) to the *A. thaliana* A3 and A9 genes, or fragments of them of, for example, 10, 20, 50 or 100 nucleotides. A 15–20 nucleotide probe would be appropriate under many circumstances.

The preferred A3 and A9 promoters described in this specification are from *Arabidopsis thaliana* and can be isolated by methods known in the art, for example by (a) synthesising cDNA from mRNA isolated from the stamens of the plant *Brassica napus*, (b) isolating this cDNA, (c) using this cDNA as a probe to identify regions of the plant genome of *Arabidopsis thaliana* that encode stamen-specific mRNA and (d) identifying the upstream (5') regulatory regions that contain the promoter of this DNA. This procedure also demonstrates that probes based on, or derived from, the coding regions of a stamen-specific DNA from one species of plant may be used to isolate DNA sequences encoding stamen-specific mRNAs from other species. A3 and A9 promoters from other members of the family Brassicaceae, for example from *B. napus* itself, are also included within the scope of the invention, as are those which include non-essential variations from the natural sequences.

Particularly preferred promoters are those upstream of the coding regions of the sequences shown in FIG. 4 (for the *A. thaliana* A3 gene) and FIG. 7 (for the *A. thaliana* A9 gene) as will subsequently be described in the examples. Those skilled in the art will be able to identify with sufficient precision the promoters driving the coding regions and to isolate and/or recombine DNA containing them.

Promoter-containing DNA in accordance with the invention can be used to confer male sterility on plants, particularly those belonging to the family Brassicaceae, in a variety of ways as will be discussed below. In an important embodiment of the invention, therefore, a promoter as described above is operatively linked to DNA which, when expressed, causes male sterility.

Since an effective sterility system is complete, propagation of the seed parent must proceed either by asexual means or via the pollination of the male-sterile by an isogenic male-fertile line, and the subsequent identification or selection of male sterile plants among the offspring. Where vegetative propagation is practical, the present invention forms a complete system for hybrid production. Where fertility restoration is necessary to produce a seed crop, the present invention forms the basis of a new male sterility system. In some seed crops where the level of cross pollination is high, seed mixtures may enable restoration to be bypassed. The male sterility will be particularly useful in crops where restoration of fertility is not required, such as in the vegetable *Brassica* spp., and such other edible plants as lettuce, spinach, and onions.

DNA in accordance with the invention and incorporating the A3 and/or A9 promoter can drive male sterility DNA thereby producing male sterile plants, which can be used in hybrid production. The promoters are highly tapetum specific and so the sterility DNA is only expressed in the tapetum. The control of expression is very strong and the DNA is not expressed in other cells of the plant. The system prevents the production of viable pollen grains. All transformed plants and their progeny are male sterile; there is no problem with meiotic segregation.

A construct comprising a promoter operatively linked to a male sterility DNA can be transformed into plants (particularly those of the genus *Brassica*, but also other genera such as *Nicotiana* and *Hordeum*) by methods which may be well known in themselves. This transformation results in the production of plants, the cells of which contain a foreign chimeric DNA sequence composed of the promoter and a male sterility DNA. Male-sterility DNA encodes an RNA, protein or polypeptide which, when produced or over-produced in a stamen cell of the plant, prevents the normal development of the stamen cell.

The tapetum specific promoters may be used to drive a variety of male sterility DNA sequences which code for RNAs proteins or polypeptides which bring about the failure of mechanisms to produce viable male gametes. The invention is not limited by the sequence driven, but a number of classes and particular examples of male sterility promoter-drivable sequences are preferred.

For example, the drivable male sterility DNA may encode a lytic enzyme. The lytic enzyme may cause lysis of one or more biologically important molecules, such as macromolecules including nucleic acid, protein (or glycoprotein), carbohydrate and in some circumstances lipid.

Ribonuclease (such as RNase T1) and barnase are examples of enzymes which cause lysis of RNA. Examples of enzymes which lyse DNA include exonucleases and endonucleases, whether site-specific such as EcoRI or non-site-specific. Glucanase is an example of an enzyme which causes lysis of a carbohydrate. The enzyme glucanase is naturally produced in anthers where it functions to release the young microspores from a protective coat of poly-glucan laid down before meiosis. The appearance of the enzyme activity is developmentally regulated to coincide with the correct stage of microspore development. One important attraction of glucanase as a potential sterility DNA is that plants are found in nature that are male-sterile due to mutations causing mistiming of glucanase expression and the destruction of the microspores. Two types are recognised depending on whether the appearance of glucanase activity is premature or late. The expression of many genes, including those expressed within the anther, exhibit various patterns of temporal regulation. Therefore, in order to use glucanase as a sterility DNA, the promoter chosen to drive expression of the gene must provide an appropriate developmental regulation of glucanase activity, preferably by mimicking the pattern of expression found in association with natural male-sterility. One means of achieving male sterility is to isolate the promoter from a tapetum-specific gene with the same pattern of expression as found for glucanase activity in male-sterile mutant plants. Since late expression of a glucanase is unlikely to produce sterility in plants with a functional anther glucanase gene, the sterility factor would require a promoter capable of driving transcription before the appearance of normal glucanase activity. In the RM cms mutant of *Petunia* (Izhar, S. and Frankel, R. *Theor. Appl. Genet.*, 41 104–108 (1971)) glucanase expression within the anther first appears at the end of meiotic prophase, and increases to a maximum by the completion of meiosis. This pattern of expression contrasts with that in normal Petunia plants, where glucanase activity within the anthers appears concomitantly with the breakdown of the tetrads and the release of the young microspores. The aberrant pattern of glucanase activity found in the cms mutant is thought to be responsible for the destruction of the microspores and male sterility. Thus, to mimic this mutation using a sterility DNA encoding a glucanase enzyme requires a promoter capable of driving transcription of the male sterility DNA within the anthers, and preferably within the tapetum, during the phase of anther development between prophase of meiosis and the appearance of the tetrad of microspores; the A3 and A9 promoters discussed above are therefore well suited to drive this gene. A tapetum-specific (or at least anther-specific) promoter is also advantageous since $\beta(1,3)$-glucans are found elsewhere within plants, for example in phloem sieve elements, where they presumably perform essential functions.

The spatial regulation of the enzyme should also ensure access to the target cells. Secretion into the locular space is ensured by the provision in a preferred embodiment, of a suitable signal sequence in a translational fusion with the glucanase coding sequence.

DNA encoding glucanase is advantageous as male sterility DNA, as it has no product which is cytotoxic outside the target cell. Glucanase as a male sterility DNA mimics natural systems and is inherently less destructive than for example ribonuclease, and so does not present such a problem if the promoter is slightly active in certain conditions in other cell types.

Actinidin is an example of a protease, DNA coding for which can be suitable male sterility DNA. Other examples include papain zymogen and papain active protein.

Lipases whose corresponding nucleic acids may be useful as male sterility DNAs include phospholipase $A_2$.

Male sterility DNA does not have to encode a lytic enzyme. Other examples of male sterility DNA encode enzymes which catalyse the synthesis of phytohormones, such as isopentyl transferase, which is involved in cytokinin synthesis, and one or more of the enzymes involved in the synthesis of auxin. DNA coding for a lipoxygenase or other enzymes having a deleterious effect may also be used.

Other male sterility DNAs include antisense sequences. Introducing the coding region of a gene in the reverse orientation to that found in nature can result in the down-regulation of the gene and hence the production of less or none of the gene product. The RNA transcribed from anti-sense DNA is capable of binding to, and destroying the function of, a sense RNA version of the sequence normally found in the cell thereby disrupting function. Examples of such anti-sense DNAs are the anti-sense DNAs of the A3 and A9 genes which may be produced in the anther under control of the A3 and A9 promoter. Since these genes are normally expressed in the tapetum, antisense to them may be expected to disrupt tapetal function and result in male sterility.

It is not crucial for antisense DNA solely to be transcribed at the time when the natural sense transcription product is being produced. Antisense RNA will in general only bind when its sense complementary strand, and so will only have its toxic effect when the sense RNA is transcribed. Antisense DNA corresponding to some or all of the DNA encoding the A3 or A9 gene products may therefore be produced not only while the A3 and A9 genes are being expressed. Such antisense DNA may be expressed constitutively, under the control of any appropriate promoter.

According to a further aspect of the invention, therefore, there is provided antisense nucleic acid which includes a transcribable strand of DNA complementary to at least part of the strand of DNA that is naturally transcribed in a gene encoding an 11.6 or 12.9 kDa tapetum protein in *Arabidopsis thaliana* or an equivalent protein in another member of the family *Brassicaceae*.

Antisense DNA in accordance with this aspect of the invention may be under the control of any suitable promoter which permits transcription during, but not necessarily only during, tapetum development. As indicated above, the promoter may therefore be constitutive, but the use of tapetum-specific promoters such as A3 and A9 as described above in relation to the first aspect of the invention is certainly not excluded and may be preferred for even grater control. Such antisense DNA would generally be useful in conferring male sterility on members of the family *Brassicaceae*.

A still further example of male sterility DNA encodes an RNA enzyme (known as a ribozyme) capable of highly specific cleavage against a given target sequence (Haseloff and Gerlach *Nature* 334 585–591 (1988). Like antisense DNA, ribozyme DNA (coding in this instance for a ribozyme which is targeted against the RNA encoded by the A3 or A9 gene) does not have to be expressed only at the time of expression of the A3 and A9 genes. Again, it may be possible to use any appropriate promoter to drive ribozyme-encoding DNA, including one which is adapted for constitutive expression.

According to a further aspect of the invention, there is therefore provided DNA encoding a ribozyme capable of specific cleavage of RNA encoded by a gene encoding an 11.6 or 12.9 kDa tapetum protein in *Arabidopsis thaliana* or an equivalent protein in another member of the family *Brassicaceae*. Such ribozyme-encoding DNA would generally be useful in conferring male sterility on members of the family *Brassicaceae*.

In preferred embodiments of DNA sequences of this invention, including those comprising the A3/A9 promoter-male sterility DNA construct, 3' transcription regulation signals, including a polyadenylation signal, may be provided. Preferred 3' transcription regulation signals are derived from the Cauliflower Mosaic Virus 35S gene. It should be recognised that other 3' transcription regulation signals could also be used.

The antisense nucleic acid and ribozyme-encoding nucleic acid described above are examples of a more general principle: according to another aspect of the invention, there is provided DNA which causes (for example on its expression) selective disruption of the proper expression of the A3 and A9 genes.

Recombinant DNA in accordance with the invention may be in the form of a vector. The vector may for example be a plasmid, cosmid or phage. Vectors will frequently include one or more selectable markers to enable selection of cells transfected (or transformed: the terms are used interchangeably in this specification) with them and, preferably, to enable selection of cells harbouring vectors incorporating heterologous DNA. Appropriate start and stop signals will generally be present. Additionally, if the vector is intended for expression, sufficient regulatory sequences to drive expression will be present; however, DNA in accordance with the invention will generally be expressed in plant cells, and so microbial host expression would not be among the primary objectives of the invention, although it is not ruled out. Vectors not including regulatory sequences are useful as cloning vectors.

Cloning vectors can be introduced into *E. coli* or another suitable host which facilitate their manipulation. According to another aspect of the invention, there is therefore provided a host cell transfected or transformed with DNA as described above.

DNA in accordance with the invention can be prepared by any convenient method involving coupling together successive nucleotides, and/or ligating oligo- and/or polynucleotides, including in vitro processes, but recombinant DNA technology forms the method of choice.

Ultimately, DNA in accordance with the invention (whether (i) A3/A9 promoter plus male sterility gene, (ii) antisense DNA to A3/A9 gene or ribozyme DNA targeted to A3/A9 RNA) will be introduced into plant cells, by any suitable means. According to a further aspect of the invention, there is provided a plant cell including DNA in accordance with the invention as described above.

Preferably, DNA is transformed into plant cells using a disarmed Ti-plasmid vector and carried by *Agrobacterium* by procedures known in the art, for example as described in EP-A-0116718 and EP-A-0270822. Alternatively, the foreign DNA could be introduced directly into plant cells using an electrical discharge apparatus. This method is preferred where *Agrobacterium* is ineffective, for example where the recipient plant is monocotyledonous. Any other method that provides for the stable incorporation of the DNA within the nuclear DNA of any plant cell of any species would also be suitable. This includes species of plant which are not currently capable of genetic transformation.

Preferably DNA in accordance with the invention also contains a second chimeric gene (a "marker" gene) that enables a transformed plant containing the foreign DNA to be easily distinguished from other plants that do not contain the foreign DNA. Examples of such a marker gene include antibiotic resistance (Herrera-Estrella et al, 1983), herbicide resistance (EP-A-0242246) and glucuronidase (GUS) expression (EP-A-0344029). Expression of the marker gene is preferably controlled by a second promoter which allows expression in cells other than the tapetum, thus allowing selection of cells or tissue containing the marker at any stage of regeneration of the plant. The preferred second promoter is derived from the gene which encodes the 35S subunit of Cauliflower Mosaic Virus (CaMV) coat protein. However any other suitable second promoter could be used.

A whole plant can be regenerated from a single transformed plant cell, and the invention therefore provides transgenic plants (or parts of them, such as propagating material) including DNA in accordance with the invention as described above. The regeneration can proceed by known methods. When the transformed plant flowers it can be seen to be male sterile by the inability to produce viable pollen. Where pollen is produced it can be confirmed to be non-viable by the inability to effect seed set on a recipient plant.

The invention will now be illustrated by the following Examples. The following restriction enzyme and other abbreviations are used:

A, AccI; B, BamHI; Bg, BglII; C, ClaI; H, HincII; Hd, HindIII; K, KpnI; M, MluI; N, NotI; Nc, NcoI; Nr, NruI; P, PstI; R, RsaI; RI, EcoRI; RV, EcoRV; S, SstI; Sa, SalI; Sp, SphI; Sm, SmaI; Ss, SspI; SII, SacII; X, XhoI; Xb, XbaI.

ORF=open reading frame

BRIEF DESCRIPTION OF THE DRAWINGS

The Examples refer to the accompanying drawings, in which:

FIG. 1 shows the DNA sequence [SEQ ID NO:1] of the *B. napus* cDNA A3 together with the deduced protein sequence of the ORF contained in A3;

FIGS. 2a–2d show a comparison of the DNA sequences of the *B. napus* cDNAs E3 [SEQ ID NO:3] with the *A. thaliana* A3 [SEQ ID NO:5] gene. The underlined trinucleotides indicate the end of the ORF encoded by each sequence;

FIG. 2e shows a comparison of the putative polypeptides encoded by *B. napus* cDNAs E3 [SEQ ID NO:6] and E5 [SEQ ID NO:4] with that encoded by the *A. thaliana* A3 gene [SEQ ID NO:2];

FIG. 4 shows the DNA sequence [SEQ ID NO:7] and putative primary structure of the *A. thaliana* A3 [SEQ ID NO:8] gene. The underlined sequence is conforms to a TATA box motif;

FIG. 5 shows the DNA sequence of the *B. napus* cDNA A9 [SEQ ID NO:9] and the putative primary structure of the ORF contained in the cDNA [SEQ ID NO:10];

FIG. 7 shows the DNA sequence [SEQ ID NO:11] and putative primary structure of the *A. thaliana* A9 [SEQ ID NO:12] gene. The underlined sequence is conforms to a TATA box motif;

FIGS. 8a–8c show the DNA sequence homology between the *B. napus* A9 cDNA and the *A. thaliana* A9 gene. Underlined nucleotides indicate the position of stop codons for the ORFs contained in these sequences;

FIG. 8d shows the homology between the putative products encoded by the *B. napus* A9 cDNA and the *A. thaliana* A9 gene;

FIGS. 14a and 14b show the construction of chimeric genes between the A3 and A9 promoters and a *N. tabacum* β-1,3 glucanase gene which lacks a C-terminal extension. FIG. 14a illustrates the preparation of transcriptional fusion constructs and FIG. 14b illustrates the preparation of translational fusion constructs.

Figure 3:
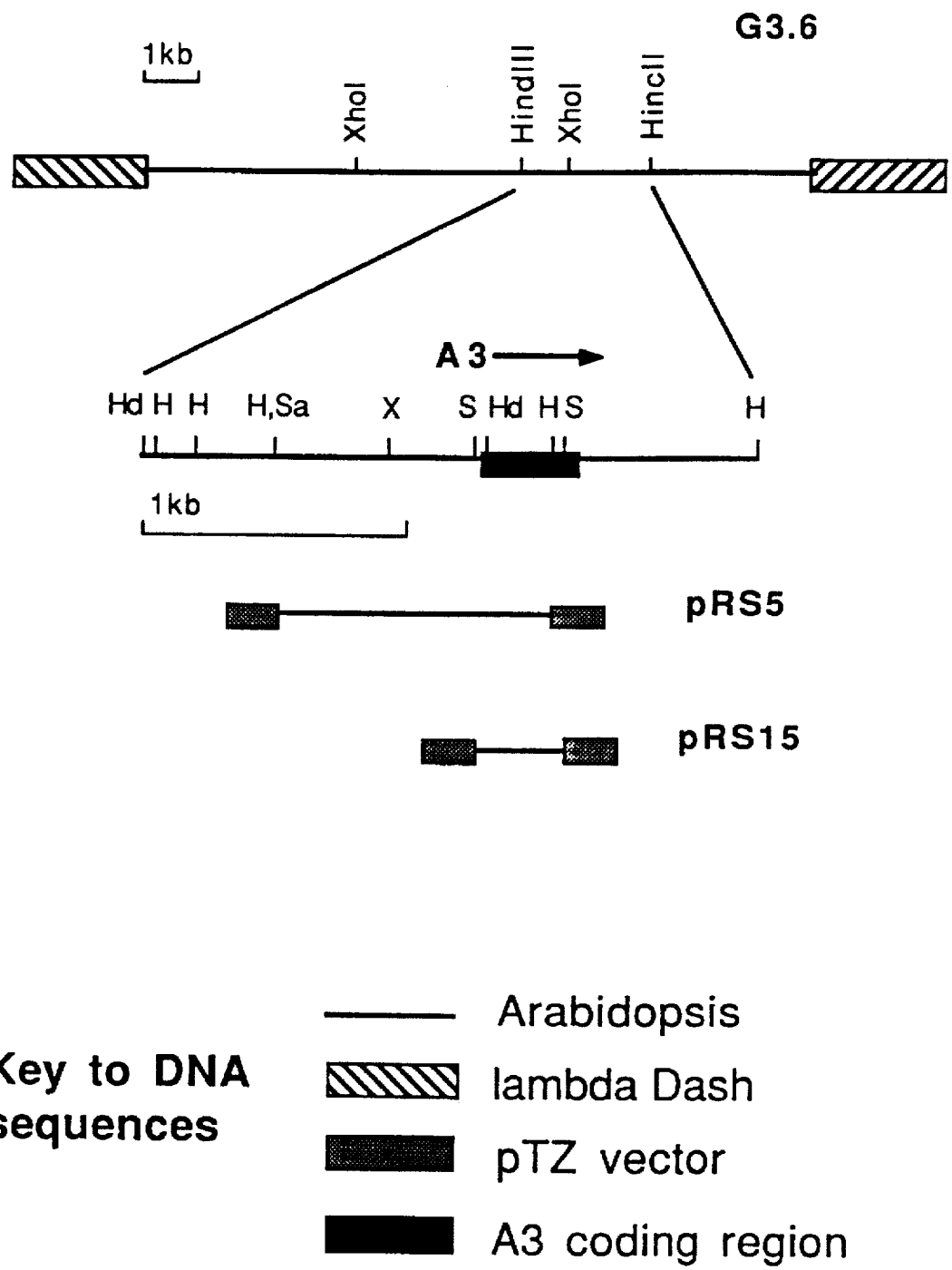
FIG. 3 shows a restriction enzyme map of the *A. thaliana* genomic clone G3.6. Only relevant sites are shown and these may not be unique in G3.6. The position of the coding region of A3 is indicated as a filled box. Also the extent of inserts cloned into the plasmids pRS5 and 15 is shown.

In the Examples, unless stated otherwise, all procedures for making and manipulating recombinant DNA were carried out using standard procedures described in Maniatis et al., Molecular Cloning: A Laboratory Manual, Cold Spring Harbor Laboratory, 1982.

DESCRIPTION OF THE PREFERRED EMBODIMENTS

EXAMPLES

Example 1

Isolation of the anther-specific genes A9 and A3 from *Arabidopsis thaliana*

Anther-specific cDNAs were isolated by differential screening of *Brassica napus* cDNA libraries constructed from RNA extracted from dissected anthers, as described below. cDNA clones A3 and A9 were isolated from a library constructed from anthers that were 1.4–1.8 mm in length. This library was constructed in the vector Lambda Zap (Stratagene). The A3 and A9 cDNAs were used as probes to isolate homologous genes from an *A.thaliana* genomic library constructed in the vector Lambda Dash (Stratagene).

Materials and Methods

Plant material. All seeding material for nucleic acid isolation was obtained from 2–3 week old plants grown in a controlled environment growth cabinet with 18 h photoperiod at 24° C. Seedling RNA for differential screening and Northern blot analysis was obtained from *B. napus oleifera* var "Topaz". Male fertile buds were collected from field grown plants of *B. napus oleifera* var. "Lictor" (Nickersons Seeds, Cambridge, UK). Male-sterile buds were obtained from field grown *B. napus* var. CMS "Ogura" (Nickersons Seeds, Cambridge, UK) plants.

Dissection of anthers. For cDNA library construction, flower spikes were quickly harvested and kept at 4° C. until required, but no longer than 5 h. Anthers were dissected from appropriately sized buds using fine forceps and immediately frozen in liquid nitrogen.

Pollen isolation. Microspores were isolated from fresh buds of the appropriate length using the method of Choung and Beaversdorf (*Plant Sci.* 39 219–226 (1985)), and frozen at −80° C. prior to RNA isolation. (Pollen isolated from frozen buds yielded only highly degraded RNA).

Collection of buds. Large samples of complete whorls of buds, at a stage immediately prior to the opening of first flowers, were frozen in liquid nitrogen and stored at −80° C.

Cytological staging of anthers and buds. The developmental stage of buds of predetermined length was assessed by light microscopic examination of sporogenous cells, microspores or pollen grains extruded from whole anthers squashed in the presence of aceto-orcein or acridine orange. Accurate determination of bud length was performed using a low-powered light microscope equipped with a calibrated eyepiece graticule. Bud lengths stated were measured from the base of the pedicle to the tip of the outermost sepal.

RNA isolation and analysis. Material intended for low resolution Northern dot blot analysis or for mRNA isolation was ground to a fine powder in a mortar cooled with liquid nitrogen. Total RNA was isolated from the powder using a phenol based method as described previously (Draper et al., "Plant Genetic Transformation and Gene Expression: A Laboratory Manual", Blackwell Scientific Publishers, Oxford (1988)). Poly(A)+ RNA was purified by two rounds of oligo(dT)-cellulose chromatography essentially as described in the Maniatis et al manual. RNA for high resolution dot blots was isolated according to the method of Verwoerd et al., Nuc. Acids Res. 17 2362 (1989)).

cDNA library construction and screening. cDNAs were synthesised from poly(A)+ RNA using (Amenham or Pharmacia) cDNA synthesis kits, according to the manufacturers instructions. cDNAs were ligated into EcoRI cleaved dephosphorylated lambda Zap I (Stratagene) ("sporogenesis" library) or lambda Zap II (Stratagene) ("microspore-development" library) and packaged using Amersham in vitro packaging extracts. Clones were screened differentially, on duplicate HYBOND-N filters (Amersham) with [$^{32}$P]-labelled single-stranded cDNA probe prepared from either the appropriate anther poly(a)+ RNA or seedling poly(A)+ RNA according to Sargent *Methods in Enzymol.* 152 423–432 (1987)). (The expression HYBOND-N is a trade mark.)

RNA dot and gel blots. Total RNA for dot-blots was spotted onto HYBOND N (Amersham) according to the manufacturers instructions. Northern gels were run and RNA transferred to HYBOND-N according to Fourney (*BRL Focus* 10 5–7 (1988)). Hybridisation and washing of HYBOND-N filters was according to manufacturers instructions.

In situ hybridisation. For embedding and sectioning *B. napus* buds were frozen in CRYO-M-BED (TAAB Laboratories Equipment Ltd). (The expression CRYO-M-BED is a trade mark.) Sections were cut nominally 10 µm thick, mounted on subbed slides (Van Prooijen-Knegt et al., *Histochemical J.* 14 333–344 (1983)) fixed in 4% paraformaldehyde and dehydrated. [$^{35}$S]rUTP (>1000 Ci/mmol, Amenham SJ.1303) labelled sense and anti-sense RNA probes were transcribed from the T3 and T7 promoters of BLUE-SCRIPT SK$^-$ (Stratagene), in which the cDNAs are cloned. (The expression BLUESCRIPT SK$^-$ is a trade mark.) Following transcription, probes were cleaved by alkaline hydrolysis to generate probe fragments approximately 150 bp in length. The hybridisation solution was 50% formamide, 300 mM NaCl, 10 mm Na$_2$HPO$_4$ pH 6.8, 10 mM Tris-HCl pH 7.5, 5 mM EDTA, 0.02% bovine serum albumin, 0.02% Ficoll, 0.02% polyvinylpyrrolidone, 10 mM dithiothreitol, 10% dextran sulphate, 0.7 mg/ml *E. coli* tRNA, 50–100 ng/ml probe stock (6.7×10$^5$ cpm/ng probe). Sections were hybridised in 30 µl hybridisation solution at 50° C. for 16 h. Slides were washed 3×1 h at 50° C. in 50% formade, 300 mM NaCl, 10 mM Na$_2$HPO$_4$ pH 6.8, 10 mM Tris-HCl pH 7.5 and then rinsed in RNase A buffer to remove formamide. RNase A treatment, (150 µg/ml RNase A in 500 mM NaCl, 10 mM Tris HCl pH 7.5), was carried out at 37° C. for 1 h. The slides were then washed twice in 2×SSC (0.3M NaCl, 0.03M Na citrate, pH 7.0) at 65° C. for 30 min, dehydrated through graded alcohols and dried. For autoradiography, slides were dipped at 45° C. in ILFORD K5 nuclear track emulsion (1 g/ml in 1:59 glycerol:water mix). (The expression ILFORD K5 is a wade mark.) Exposure time was between 2 and 14 days. Development was in KODAK D19. (The expression KODAK D19 is a trade mark.) Following development sections were stained with methylene blue and made permanent.

a) Isolation and characterisation of the *A. thaliana* A3 gene

Northern hybridisation analysis using RNA extracted from *B. napus* anthers, pollen, carpels and seedlings indicated that A3 was only expressed in anthers of length 1.6–2.3 mm with maximal expression between 1.8–2.3 mm. Thus A3 temporal expression spans the period in anther development when the microsporocytes are in meiotic division to early microspore interphase. In situ hybridisations suggest that in *B. napus*, A3 is expressed solely in the tapetum of the anther. The A3 cDNA is 347 bp in length and contains an open-reading frame (ORF) extending from position 1–329 bp (FIG. 1) suggesting that this clone is not full-length. The estimated size of *B. napus* A3 mRNA from Northern gel blots is about 500 bp, and again suggesting that this clone is not full length. The A3 cDNA was used to isolate homologous cDNA clones (E3 and E5) from the same *B. napus* library. E5 cDNA is 422 bp long and contains an ORF from position 1–333 (FIG. 2a). This cDNA is identical to A3 cDNA over the region they overlap and extends the A3 sequence 5 bp 5' of the start of A3 and 69 bp 3' of the end of A3. The E3 cDNA is 398 bp in length with an ORF extending from position 1–314 bp (FIG. 2a). The E3 cDNA is 95% identical to the E5 cDNA at the nucleotide level and the putative ORF products are 91% identical. The cloning of E5 which is homologous but not identical to A3 is evidence that probes based on the sequence of the anther-specific gene A3 would enable the cloning of homologous anther-specific genes.

A 15 kb *A. thaliana* genomic clone (G3.6) was isolated that hybridises to A3 cDNA (FIG. 3). The 2300 bp HindIII-HincII region which hybridised strongly with the A3 probe, was subcloned from G3.6 and partially sequenced (FIG. 4) revealing an ORF (positions 770–1126) that is highly homologous to the *B. napus* E5 cDNA (82% at the nucleotide level and 76% at the protein level) (FIGS. 2a,b). The *A. thaliana* A3 gene does not apparently contain introns. The putative protein encoded by A3 consists of 118 amino-acids with a molecular mass of 12.9 kDa. A search of the NBRF protein database (release 34) did not reveal any proteins homologous to the putative A3 protein. There is a TATA box consensus sequence (Joshi, 1987) between positions 699–707 bp, 63 bp upstream of the putative start of the A3 coding region.

b) Isolation and characterisation of the A9 gene

Northern analysis and in situ hybridisations indicate that the *B. napus* A9 gene is expressed in the tapetal cells of anthers of length 1.5–2.3 mm, with maximal expression between 2.0–2.3 mm. Expression of A9 is initiated in anthers that contain meiocytes and continues into anthers that contain microspores in early first interphase. The A9 cDNA is 490 bp in length containing an ORF from position 1–296 bp (FIG. 5). From Northern gel blots, the estimated size of the A9 mRNA in *B. napus* is about 550–600 bp. The abundance of the A9 mRNA was estimated at between 0.1–0.2% of total anther polyA+ mRNA.

Figure 6:
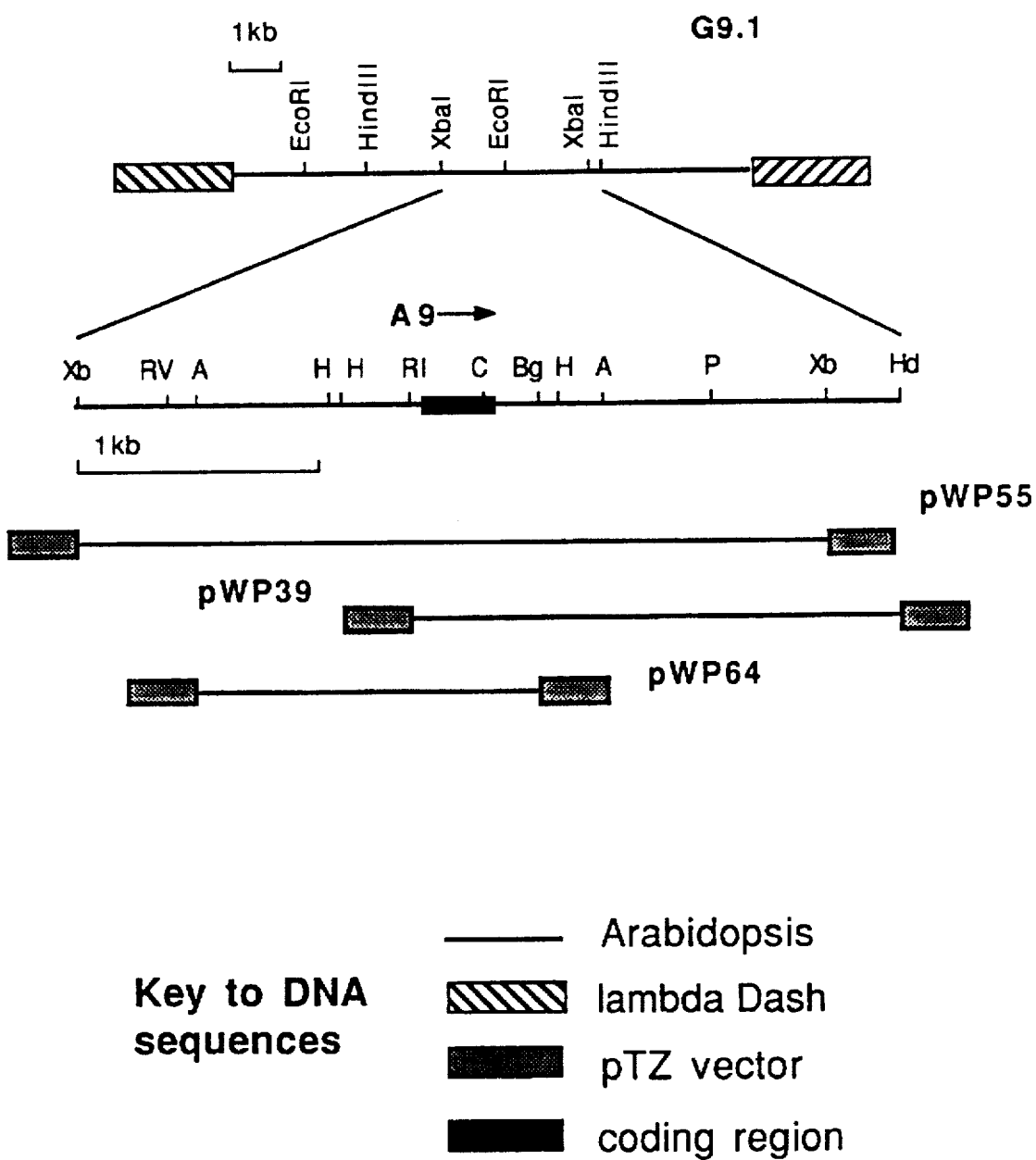
FIG. 6 shows a restriction map of the *A. thaliana* genomic clone G9.1. The position of the A9 coding region is shown as a filled box and the extent of inserts in the plasmids pWP39, 55 and 64 is indicated.

A 13 Kb *A. thaliana* genomic clone (G9.1) was isolated that hybridised to the A9 cDNA (FIG. 6) and a 3145 bp XbaI fragment cloned and partially sequenced (FIG. 7). This fragment contains an ORF at position 1461–1781 that is 76% identical to the A9 cDNA ORF at the nucleotide level (FIG. 8a) and the putative products of these ORFs are 73% identical (FIG. 8b). Comparison of the cDNA and genomic sequences suggests that the ORF in the cDNA starts at position 9 bp (FIG. 5) and that the A9 gene contains no introns. 70 bp upstream of the putative start of the A9 gene (positions 1382–1389 bp) is a TATA box conforming to the consensus sequence of Joshi (1987). The putative ORF encoded by the *B. napus* cDNA is 96 amino-acids in length with a calculated molecular mass of 10.3 kDa and that of the *A. thaliana* gene 107 amino-acids with a mass of 11.6 kDa. Although no overall homology was found to the putative A9 proteins by searching the NBRF protein database the A9 protein contains a cysteine motif that is present in several 2S plant storage proteins and in some plant protease inhibitors.

Example 2

The use of the A9 and A3 promoters to drive the expression of β-glucuronidase in anthers of *Arabidopsis thaliana* and *Nicotiana tabacum*.

Figure 9:
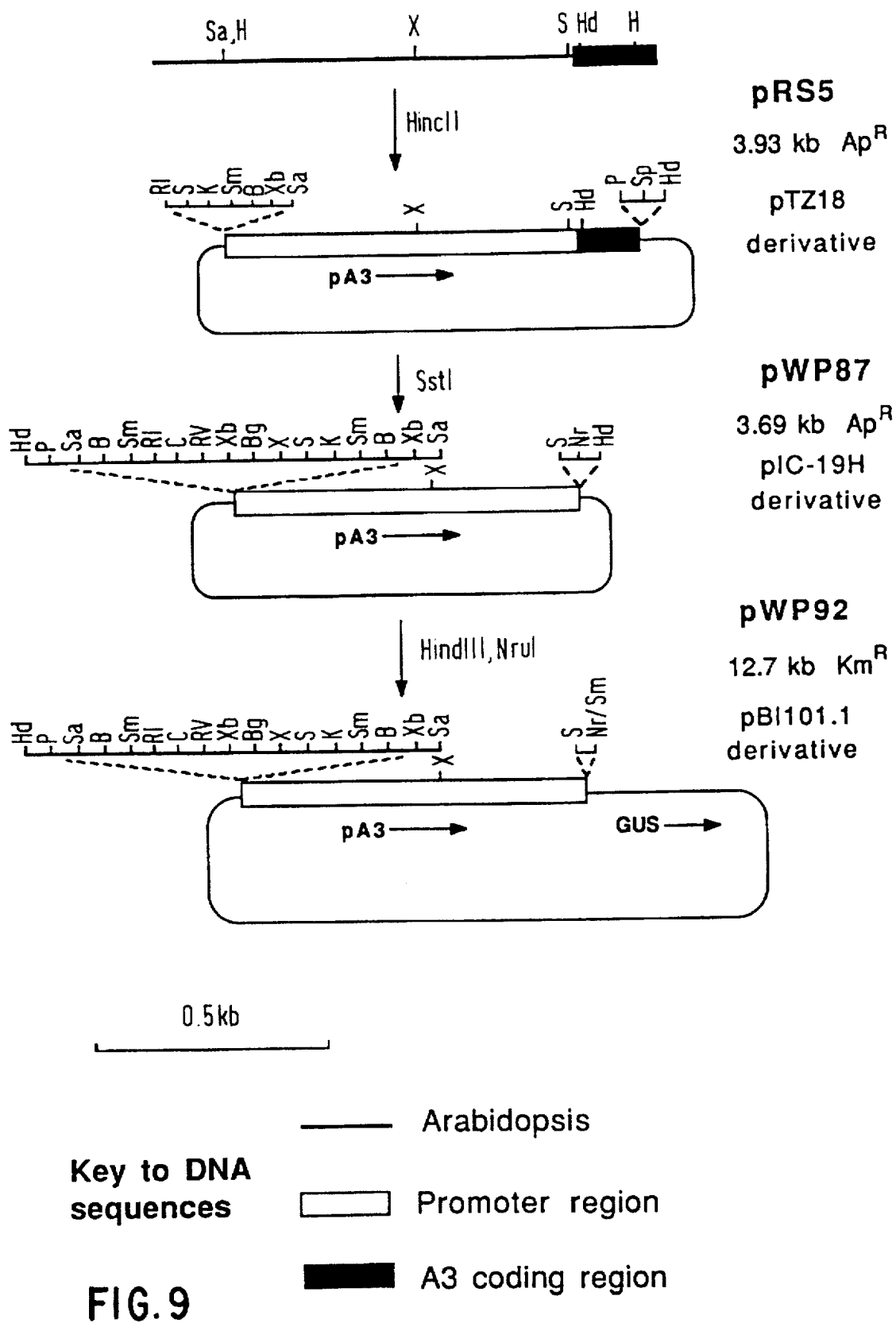
FIG. 9 shows the construction of a chimeric gene containing a transcriptional fusion between the A3 promoter and an *E. coli* gene encoding β-glucuronidase.

To demonstrate that the putative promoter regions of A3 and A9 are capable of driving the expression of a foreign gene in *A. thaliana* and *N. tabacum*, transcriptional fusions of the promoters were made to the *Escherichia coli* gene encoding β-glucuronidase (GUS).

a) A3 -GUS fusion (FIG. 9)

Figure 10:
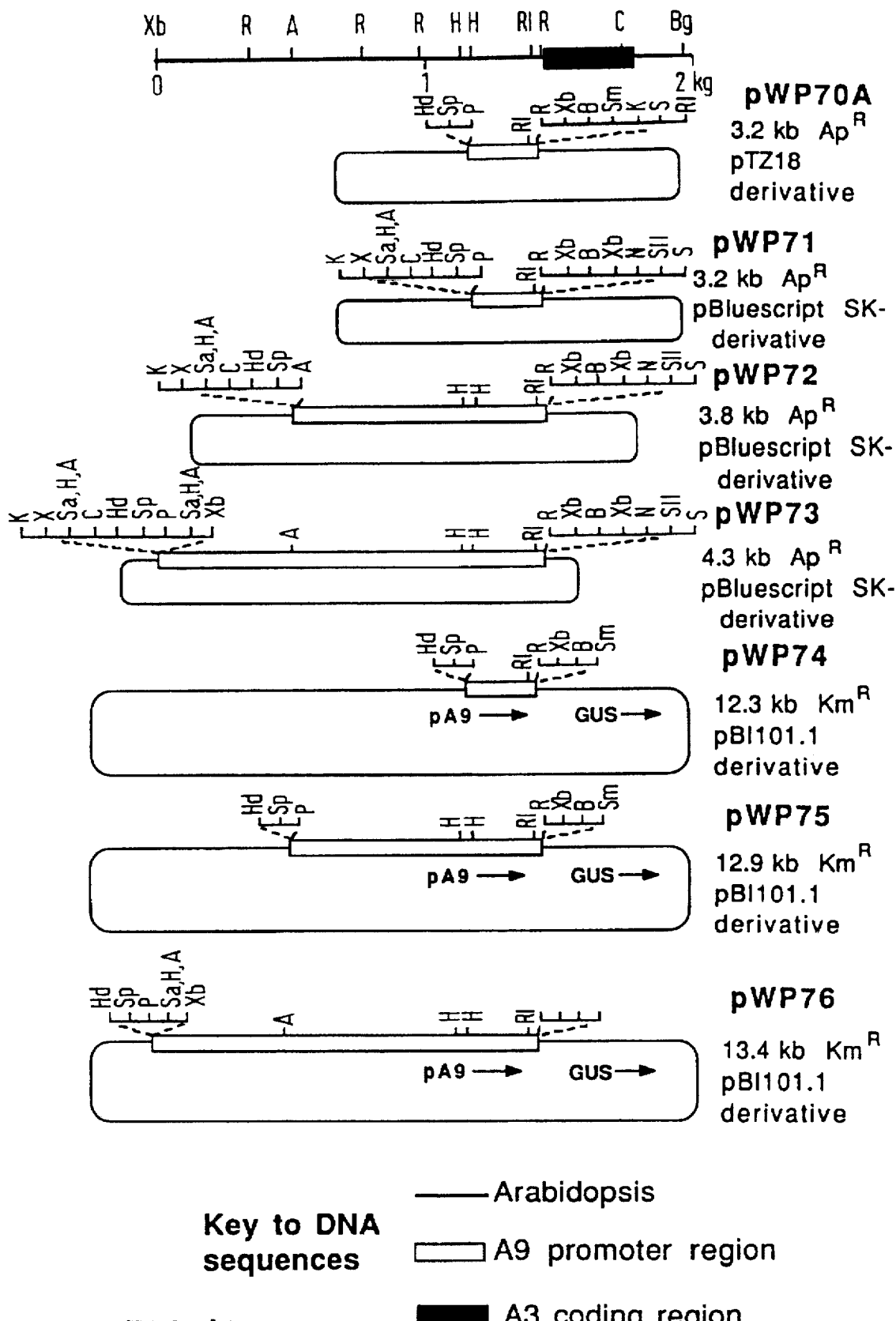
FIG. 10 shows the construction of chimeric genes containing transcriptional fusions between the A9 promoter and an *E. coli* gene encoding β-glucuronidase.

The 1030 bp HincII fragment of G3.6 is subcloned between into the HincII site of the vector pTZ18 (Pharmacia Ltd.) forming pRS5 (FIG. 9). This is cut with SstI and the fragment cloned into SstI-cut pIC19H (Marsh et al., *Gene* 32 481–485 (1984)) forming pWP87. The A3 promoter is then recovered as a HindIII-NruI fragment from pWP87 and cloned into HindIII, SmaI-cut pBI101.1 (Jefferson et al., *EMBO J* 6 3901 (1987)). The resultant plasmid (pWP92) (FIG. 9) contains 745 bp of A3 sequence upstream of the SstI site (position 745 bp in FIG. 4) fused to GUS.

b) A9-GUS fusions (FIG. 10)

The 329 bp HincII-RsaI fragment (positions 1105–1434 bp in FIG. 7) was cloned into HincII-cut pTZ18 forming pWP70A. DNA sequence analysis revealed the loss of a 'G' residue at the RsaI, HincII junction which resulted in the recreation of the RsaI site. The HindIII, BamHI fragment of pWP70A containing the A9 promoter was cloned into BamHI, HindIII-cut pBluescript (Stratagene) forming pWP71. To reconstruct plasmids with larger A9 upstream regions the EcoRI, HindIII fragment of pWP71 was replaced with the 900 bp HindIII, EcoRI fragment of pWP64 (FIG. 6) (which contains a 1486 bp AccI, BglII fragment cloned into AccI, BamHI-cut pTZ19) forming pWP72. Also the EcoRI, HindIII fragment of pWP71 was replaced with the 1397 bp HindIII, EcoRI fragment of pWP55 (FIG. 6) (which contains a 3146 bp XbaI fragment cloned into XbaI-cut pTZ19) forming pWP73. The HindIII, XbaI fragments of pWP71, pWP72 and pWP73 were cloned into HindIII, XbaI-cut pBI101.1 forming pWP74, pWP75 and pWP76 respectively. Thus pWP74 contains a 329 bp A9 promoter fragment (positions 1108–1437 bp), pWP75 a 936 bp A9 fragment (positions 501–1437 bp) and pWP76 a 1437 bp A9 fragment (positions 1–1437 bp) all fused to GUS.

Figure 11:
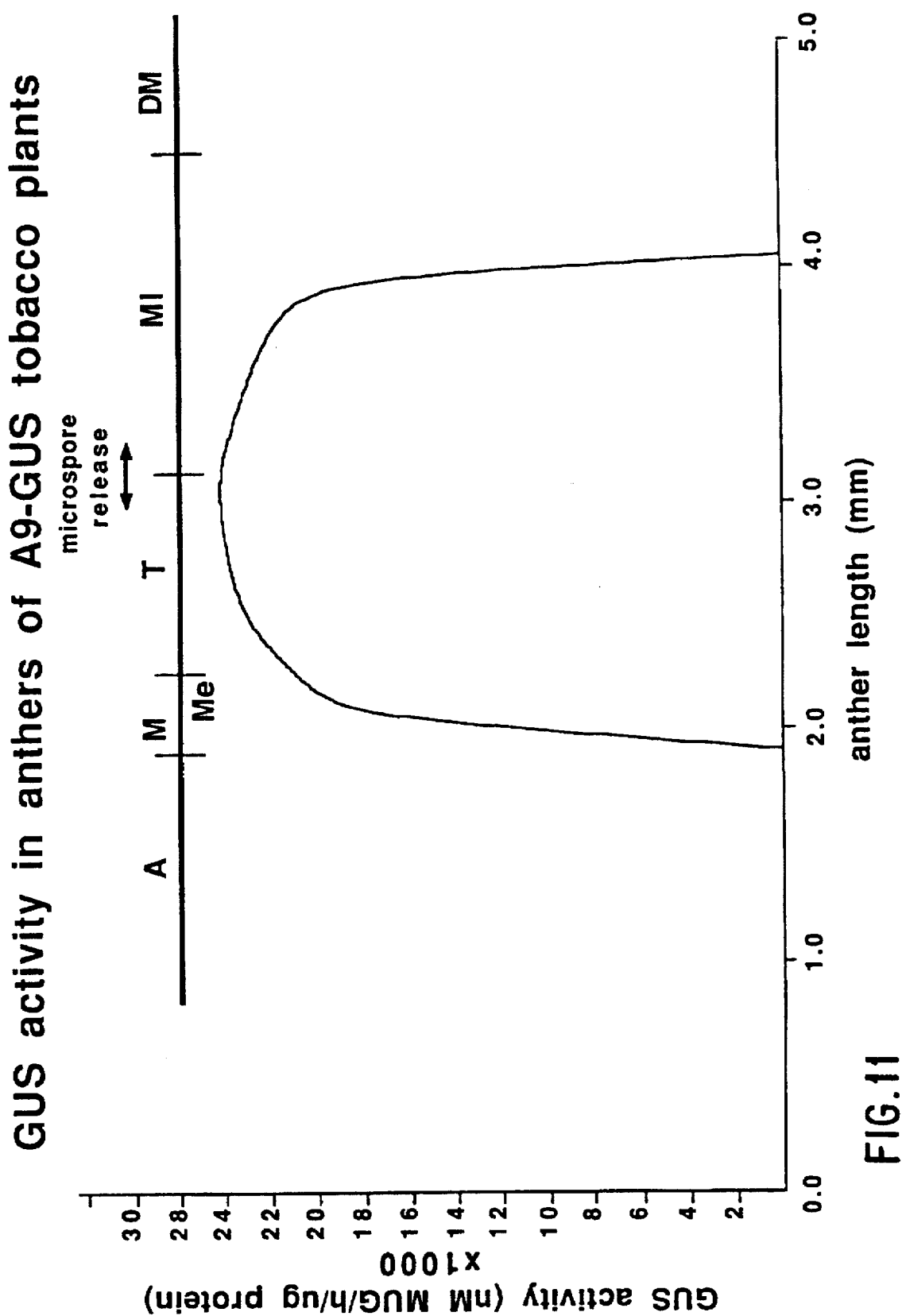
FIG. 11 shows β-glucuronidase activity in anthers of A9-GUS transformed tobacco plants.

All the GUS constructs are then transformed into *N. tabacum* and *A. thaliana* using standard transformation techniques. Analysis of transformed plants demonstrated that GUS activity was localised to anther tissues, specifically to tapetal cells. The temporal regulation of GUS activity was identical to the temporal expression observed for the A3 and A9 genes as described in Example 1. FIG. 11 shows the activity of the A9-GUS fusions in the anthers of transgenic tobacco plants. GUS activity was assayed fluorometrically in the anthers staged precisely in terms of the development of the sporogenous cells. The pattern of expression of GUS was the same (quantitatively and qualitatively) irrespective of the length of upstream region employed in the fusion. These experiments clearly demonstrate that the A9 promoter drives transcription in tapetal cells through a period commencing at the meiocyte stage of development and terminating during early microspore interphase.

Example 3

The construction of expression cassettes and their use in producing sense and anti-sense RNA to anther-specific messages in transgenic plants.

Figure 12:
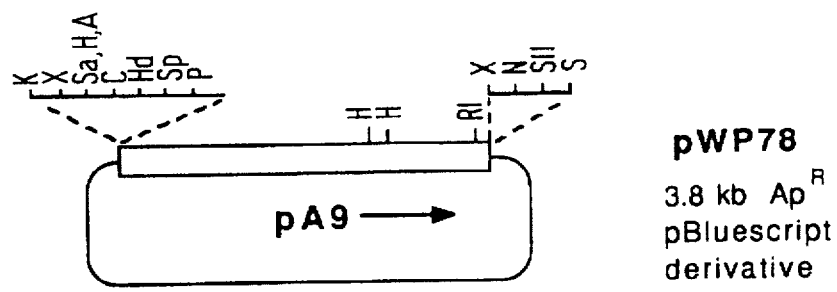
FIG. 12 shows the construction of intermediate cloning vectors used in the production of chimeric genes that express sense and anti-sense RNA from the A3 and A9 promoters in transgenic plants.
Figure 12:
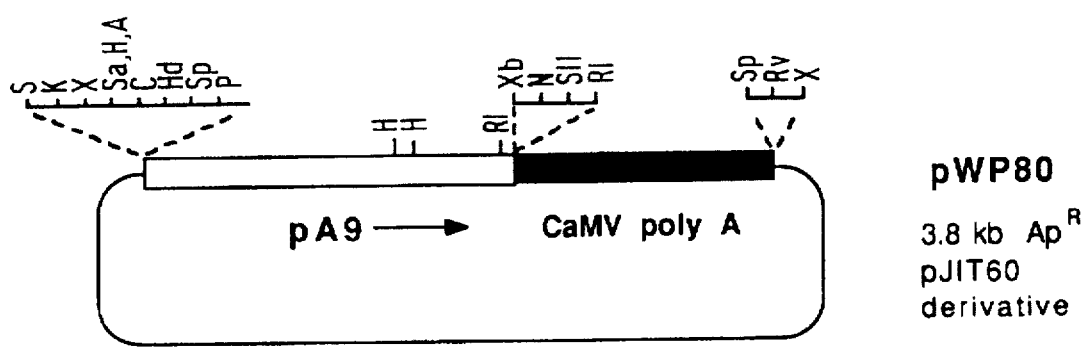
Figure 12:
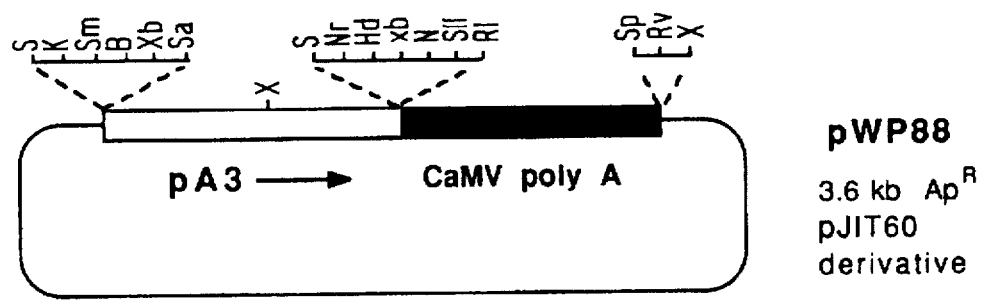

Either anther-specific or constitutive promoters can be used to drive the expression of sense or anti-sense RNA corresponding to anther-specific transcripts in transgenic plants, thus potentially creating anther mutations and male-sterility. The same anther-specific promoters can be used to drive the anther-specific expression of genes encoding proteins or enzymes detrimental to anther function thereby creating male-sterility. The use of the expression cassettes, the construction of which is described in this example, for this application are described in Examples 4 and 5.

a) Construction of an intermediate vector to express sense and anti-sense RNA utilising the A9 promoter.

pWP72 (FIG. 10) is digested with XbaI and religated, thus removing the BamHI site in the polylinker, forming pWP78 (FIG. 12). The KpnI, SstI (the SstI end rendered blunt with Klenow) A9 promoter fragment of pWP78 is ligated into KpnI, SmaI-cut pJIT60 forming pWP80 (FIG. 12). pJIT60 is identical to pJIT30 (Guerineau et al., *Plant Mol. Biol.* 15, 127–136 (1990)) except that the CaMV 35S promoter is replaced by a double CaMV 35S promoter (Guerineau et al., *Nuc. Acids Res.* 16 (23) 11380 (1988)). The pWP80 intermediate vector consists of a 936 bp A9 promoter fragment fused to a polylinker derived from pBluescript with a 35S CaMV polyadenylation signal to stabilise the transcript.

b) Construction of an intermediate vector to express sense and anti-sense RNA utilising the A3 promoter.

The CaMV promoter of pJIT60 is replaced with the A3 promoter by cloning the 745 bp KpnI, HindIII fragment of pWP87 (FIG. 9) into KpnI, HindIII-cut pJIT60 forming pWP88 (FIG. 12). pWP80 and pWP88 are therefore identical apart from the promoter region and surrounding restriction enzyme sites.

c) Construction of chimeric genes containing the tapetum-specific A9 promoter linked to the sense or anti-sense orientation of the A9 cDNA.

Anther-specific *B. napus* cDNAs were cloned into EcoRI-cut Lambda ZapII by the addition of EcoRI linkers (Pharmacia Ltd) to the ends of the cDNA. These linkers aim contain internal NotI sites, so the entire cDNA can be recovered as a NotI fragment provided the cDNA contains no internal NotI sites. The *B. napus* cDNA for A9 is therefore recovered as a NotI fragment and cloned in both orientations (sense and anti-sense) into NotI-cut pWP80. The promoter, cDNA and terminator regions are excised from the pWP80 derivatives with a HindIII, XhoI digest and are cloned into SalI, HindIII-cut pBin19 (Bevan et al., *Nuc. Acids Res.* 22 8711–8721 (1984)).

The pBin19 derivatives are transformed into *B. napus*. The resulting transgenic plants expressing anti-sense A9 RNA are male sterile.

Other chimeric genes that can be constructed to produce male sterility are:

i) A9 promoter linked to the coding region of the *A. thaliana* A9 gene, such that anti-sense A9 RNA is expressed;

ii) A3 promoter driving expression of anti-sense A9, either from the A9 cDNA or from the *A. thaliana* A9 gene;

iii) A9 promoter expressing anti-sense RNA to A3, using either the A3 cDNA or the *A. thaliana* A3 gene;

iv) A3 promoter expressing anti-sense RNA to A3, using either the A3 cDNA or the *A. thaliana* A3 gene.

These plasmids could also be transformed into other members of the *Brassicaceae* causing male sterility in the transgenic plants.

Example 4

Construction of chimeric A3-barnase and A9-barnase genes and their expression in transgenic plants.

To demonstrate the utility of the A3 and A9 promoters they are used to drive the expression of the RNase, barnase, in tapetal cells. Use of the barnase gene to create male sterile plants has been described in EP-A-0344029 (Plant Genetic Systems) and has been published by Mariani et al., *Nature* 347, 737–741.

Figure 13A:
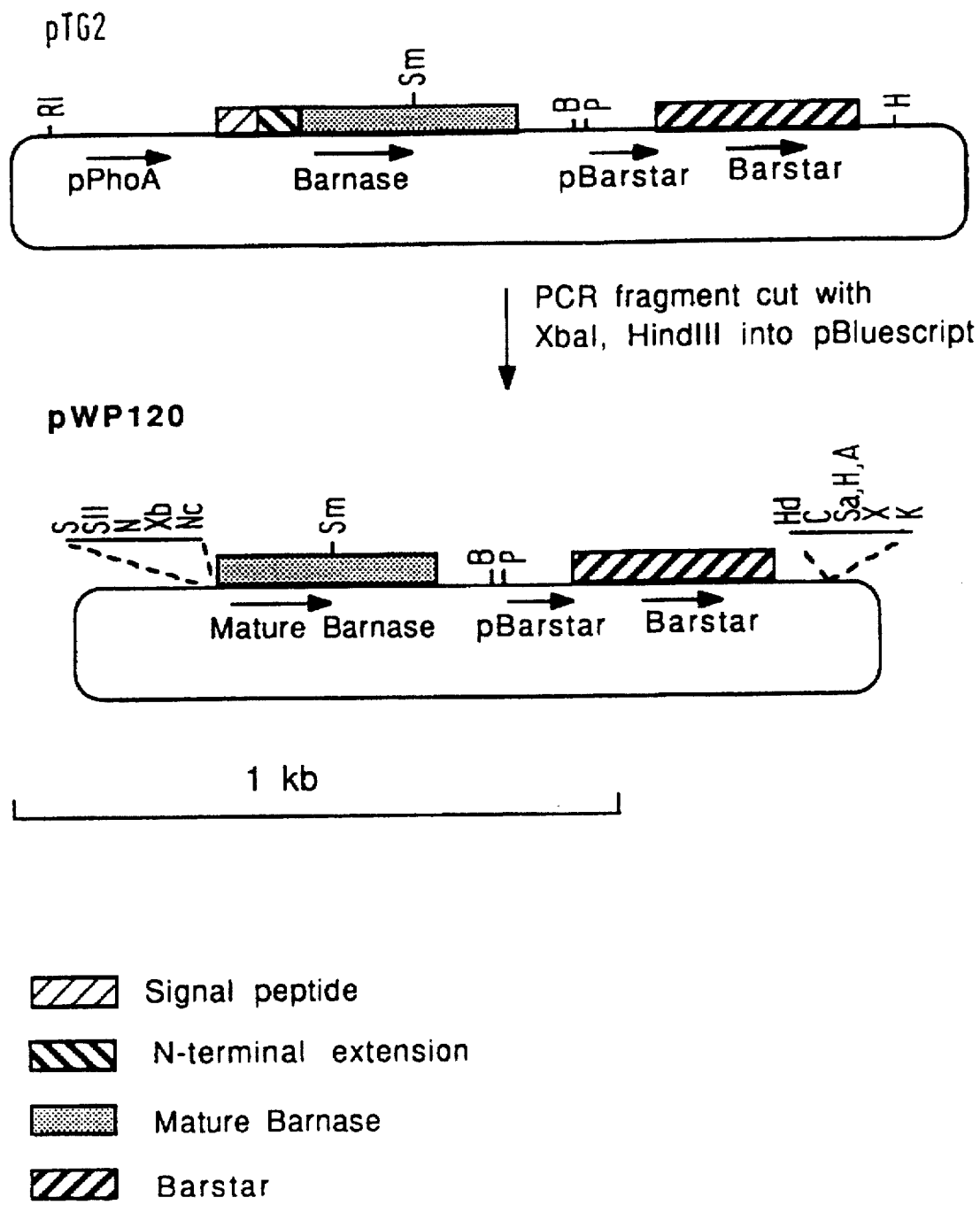
FIGS. 13a and 13b show the construction of chimeric genes between the A3 and A9 promoters and the RNAse barnase.

The oligonucleotide primers [SEQ ID NO:13] and [SEQ ID NO:14]:

```
5' GGGTCTAGACCATGGCACAGGTTATCAACACGTTTGACGG 3'  and
5' GTAAAACGACGGCCAGTGCC 3'
``` are used in a polymerase chain reaction (PCR) to generate a fragment encoding barstar and the mature barnase product from the plasmid pTG2 (Horovitz et al., *J. Mol. Biol.* 216, 1031–1044 (1990)). The first primer is homologous to nucleotides 95–221 bp of FIG. 1 in Hartley R. W. *J. Mol. Biol.* 202, 913–915 (1988). The second primer is homologous to a sequence immediately next to the HindIII site of pTZ18U (Pharmacia). Barstar is retained on this fragment since active barnase cannot be cloned in the absence of the specific inhibitor barstar (only barnase is expressed in the transgenic plants). The PCR fragment is digested with XbaI, HindIII and cloned into XbaI, HindIII-cut pBluescript forming pWP120 (FIG. 13a).

a) Transcriptional fusion of the A9 promoter to barnase pWP120 is digested with XbaI, HincII and the barnase/barstar fragment cloned into XbaI-SmaI cut pWP91 forming pWP127 in which the A9 promoter is transcriptionally fused to the mature barnase sequence (FIG. 13b) (pWP91 is identical to pWP80 except that the polylinker region between XbaI and EcoRI has been replaced with the sites SpeI, BamHI, SmaI and PstI). This gene fusion is transferred to pBin19 by ligating the XhoI fragment-of pWP127 to SaII-cut pBin19.

b) Translational fusion of the A9 promoter and gene to barnase

The primers [SEQ ID NO:15] and [SEQ ID NO:16]

Figure 13B:
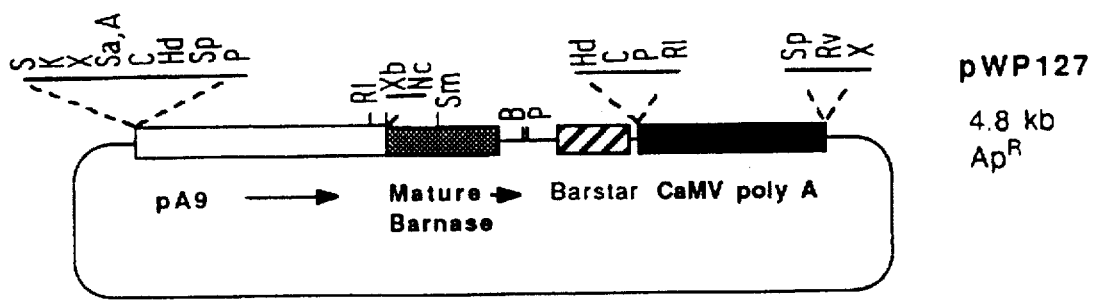
Figure 13B:
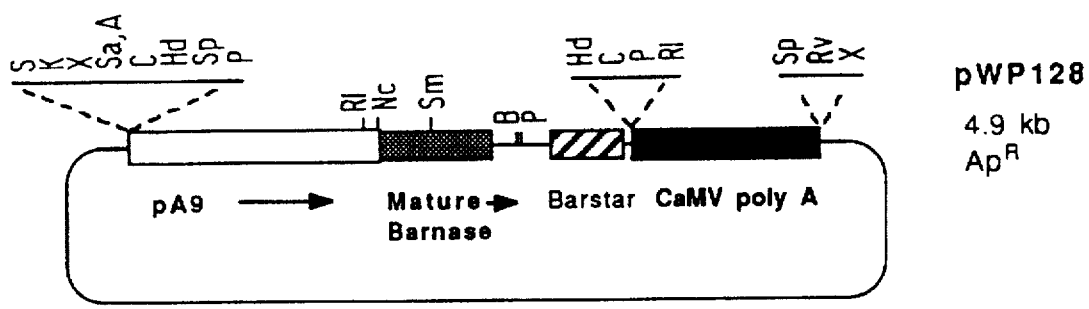
Figure 13B:
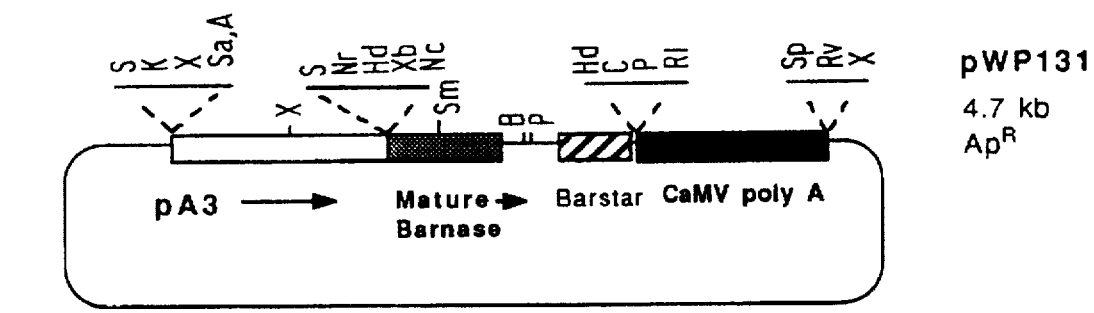

```
5' GGGTCTAGACCATGGTAATTAGATACTATATTGTTTGTAC 3'  and
5' AATACGACTCACTATAGG 3'
``` are used in a PCR reaction to generate an A9 promoter fragment from pWP64 (FIG. 6) that contains the entire 5' untranslated region of the A9 gene and has the sequence around the initiating methionine of the A9 gene mutated to an NcoI site (the second primer is homologous to a sequence within the pTZ19U vector). This fragment is cut with HindIII, XbaI and cloned into pWP80 or pWP91 replacing the existing A9 promoter fragments in these intermediate vectors. The new intermediate vectors are pWP112 and pWP113 respectively.

pWP120 is cut with NcoI, HincII and the barnase/barstar fragment cloned into NcoI, SmaI-cut pWP113 forming pWP128 (FIG. 13b). The chimeric gene is then cloned as an XhoI fragment into the SalI site of pBin19.

c) Transcriptional fusion of the A3 promoter to barnase

The A9 promoter of pWP127 is replaced with the A3 promoter by cutting pWP127 with SalI, XbaI and cloning in the SalI, XbaI A3 promoter fragment of pWP88 forming pWP131 (FIG. 13b). The chimeric gene is transferred as a KpnI, XhoI fragment into KpnI, SalI-cut pBin19.

The pBin19 derivative plasmids are transformed into *N. tabacum* where expression of barnase in transgenic plants results in the degradation of the tapetal cells of the anther causing complete male sterility. The plants are female fertile. Thus both the A3 and A9 promoters are tapetum-specific and are suitable for driving the expression of any cytotoxic agent within tapetal cells leading to the production of male sterile, but otherwise phenotypically normal transgenic plants. These plasmids could also be transformed into other crop species such as *B. napus*, *Zea mays* and *Hordeum vulgare* leading to male sterility in the transgenic plants.

Example 5

Construction and expression in transgenic plants of chimeric gene fusions between the A3 and A9 promoters and a β-1,3 glucanase gene.

The temporal pattern of expression of the A3 and A9 genes determined from Northern analysis (Example 1) and promoter-GUS fusions (Example 2) show that both promoters are active at stages of anther development prior to the release of microspores from tetrads. Thus either promoter is suitable for driving the premature expression of β-1,3 glucanase in anthers leading to male sterility, as previously discussed.

cDNAs encoding an *N. tabacum* basic β-1,3 glucanase has been described by Shinshi et al. (*PNAS* 85 5541–5545 (1988)) and Neale et al. (*Plant Cell* 2 673–684 (1990)). This enzyme is located in the vacuole and it has been suggested that a C-terminal sequence may be responsible for its intracellular location (Van den Bulcke et al., *PNAS* 86 2673–2677 (1989)). An engineered cDNA for this glucanase is cloned by using two oligonucleotides complementary to the sequence of an *N. tabacum* glucanase (Shinshi et al., 1988, Neale et al., 1990) and using the polymerase chain reaction to isolate a glucanase cDNA from *N. tabacum* mRNA. The first oligonucleotide has sequence [SEQ ID NO:17]:

```
5' CGCTCTAGACCATGGCTGCTATCACACTCCTAGG 3'
```

This primer contains an XbaI and an NcoI site followed by a sequence identical to a 5' region of glucanase (positions 7–29 in Shinshi et al., 1989). The second oligonucleotide has sequence [SEQ ID NO:18]:

```
5' GGGCCGCGGTCACCCAAAGTTGATATTATATTTGGGC 3'
```

This primer has a SacII site followed by a trinucleotide that is a stop codon and a sequence complementary to the region that encodes the C-terminus of the mature glucanase (positions 1017–993 in Shinshi et al., 1988). The glucanase is therefore cloned with restriction enzyme sites at both ends for ligation into the intermediate vectors pWP80 and pWP88. Also the enzyme is been engineered so that the C-terminal targeting signal is removed. The enzyme will therefore be secreted rather than be directed to the vacuole when expressed in transgenic plants. The glucanase gene is cloned as an XbaI, SacII fragment into XbaI, SacII-cut pWP80 forming a transcriptional fusion between the A9 promoter and glucanase forming pDW80PR. An A3-glucanase transcriptional fusion is constructed by replacing the SalI, XbaI A9 promoter region of pDW80PR with the SalI, XbaI A3 promoter fragment of pWP88 forming pDW88PR (FIG. 14a). A translational fusion of the A9 promoter and gene to the glucanase is made by cloning the glucanase as an NcoI, SacII into NcoI, SacII-cut pWP112 forming pDW112PR (FIG. 14b). The chimeric genes in pDW80PR and pDW112PR are transferred as SacI, EcoRV fragments into SalI, SmaI-cut pBin19 and the chimeric gene in pDW88PR transferred as a SalI, EcoRV fragment into SalI, SmaI-cut pBin19. The pBin19 derivatives are transformed into N. tabacum. Callose surrounding the microsporocytes prematurely disappears in the transgenic plants causing male sterility. These plasmids could also be transformed into other crop species such as B. napus, Zea mays and Hordeum vulgare leading to male sterility in the transgenic plants.

---

SEQUENCE LISTING ( 1 ) GENERAL INFORMATION:

( i i i ) NUMBER OF SEQUENCES: 18

( 2 ) INFORMATION FOR SEQ ID NO: 1:

( i ) SEQUENCE CHARACTERISTICS:
( A ) LENGTH: 347 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: CDS
( B ) LOCATION: 3..329
( D ) OTHER INFORMATION: /codon_start=3
/ product="Bn A3 gene"

( x i ) SEQUENCE DESCRIPTION: SEQ ID NO: 1:

```
TT TCT TCT TTC TGT TTA CTC CTC CTC GTC GTC TTC TTC CTC AAT TCT              47
   Ser Ser Phe Cys Leu Leu Leu Leu Val Val Phe Phe Leu Asn Ser
   1               5                   10                  15

CAA CCT GCA CTC TCA CTC CGT GTC CCA AAA CCG CAG TCA GAA CCA GCA             95
Gln Pro Ala Leu Ser Leu Arg Val Pro Lys Pro Gln Ser Glu Pro Ala
                20                  25                  30

TCA CCA CAA ACC ATG ATC GAT GAC TCA TCT CCA ATG GGA ATG ATC GAC            143
Ser Pro Gln Thr Met Ile Asp Asp Ser Ser Pro Met Gly Met Ile Asp
            35                  40                  45

CAT GCA AAG TCC ATG ATT GCT GGA TTC TTC AGC CAC AAG TTT CCA GTA            191
His Ala Lys Ser Met Ile Ala Gly Phe Phe Ser His Lys Phe Pro Val
        50                  55                  60

ATG GGC TGG CCT TTC CCC AAG TAC CCA CCT TTC ACA ATG GTC AAC CCT            239
Met Gly Trp Pro Phe Pro Lys Tyr Pro Pro Phe Thr Met Val Asn Pro
    65                  70                  75

AAC GTT CCA ACA AAC CCA TCT GGA GCT CAA GAG GAA TCA GAG AAG CTA            287
Asn Val Pro Thr Asn Pro Ser Gly Ala Gln Glu Glu Ser Glu Lys Leu
80                  85                  90                  95

CCT TCT TCC CCA AGC AAA CTT AAC AAA GCT GGA CGA AAC GCA                    329
Pro Ser Ser Pro Ser Lys Leu Asn Lys Ala Gly Arg Asn Ala
                100                 105

TGAAAATTGT TGTTGGAA                                                         347
```

( 2 ) INFORMATION FOR SEQ ID NO: 2:

( i ) SEQUENCE CHARACTERISTICS:
( A ) LENGTH: 109 amino acids
( B ) TYPE: amino acid
( D ) TOPOLOGY: linear ( i i ) MOLECULE TYPE: protein ( i x ) FEATURE:

( D ) OTHER INFORMATION: product="Bn A3 amino acid"

( x i ) SEQUENCE DESCRIPTION: SEQ ID NO: 2:

```
Ser Ser Phe Cys Leu Leu Leu Leu Val Val Phe Phe Leu Asn Ser Gln
 1               5                   10                  15

Pro Ala Leu Ser Leu Arg Val Pro Lys Pro Gln Ser Glu Pro Ala Ser
                20                  25                  30

Pro Gln Thr Met Ile Asp Asp Ser Ser Pro Met Gly Met Ile Asp His
            35                  40                  45

Ala Lys Ser Met Ile Ala Gly Phe Phe Ser His Lys Phe Pro Val Met
     50              55                  60

Gly Trp Pro Phe Pro Lys Tyr Pro Pro Phe Thr Met Val Asn Pro Asn
 65              70                  75                      80

Val Pro Thr Asn Pro Ser Gly Ala Gln Glu Glu Ser Glu Lys Leu Pro
                85                  90                  95

Ser Ser Pro Ser Lys Leu Asn Lys Ala Gly Arg Asn Ala
                100                 105
```

( 2 ) INFORMATION FOR SEQ ID NO: 3:

( i ) SEQUENCE CHARACTERISTICS:
        ( A ) LENGTH: 422 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 2..334
        ( D ) OTHER INFORMATION: /codon_start=2
                            / product="Bn E5 gene"

( x i ) SEQUENCE DESCRIPTION: SEQ ID NO: 3:

```
A AAG GTT TCT TCT TTC TGT TTA CTC CTC CTC GTC GTC TTC TTC CTC        46
  Lys Val Ser Ser Phe Cys Leu Leu Leu Leu Val Val Phe Phe Leu
   1               5                   10                  15

AAT TCT CAA CCT GCA CTC TCA CTC CGT GTC CCA AAA CCG CAG TCA GAA      94
Asn Ser Gln Pro Ala Leu Ser Leu Arg Val Pro Lys Pro Gln Ser Glu
                20                  25                  30

CCA GCA TCA CCA CAA ACC ATG ATC GAT GAC TCA TCT CCA ATG GGA ATG     142
Pro Ala Ser Pro Gln Thr Met Ile Asp Asp Ser Ser Pro Met Gly Met
                35                  40                  45

ATC GAC CAT GCA AAG TCC ATG ATT GCT GGA TTC TTC AGC CAC AAG TTT     190
Ile Asp His Ala Lys Ser Met Ile Ala Gly Phe Phe Ser His Lys Phe
            50                  55                  60

CCA GTA ATG GGC TGG CCT TTC CCC AAG TAC CCA CCT TTC ACA ATG GTC     238
Pro Val Met Gly Trp Pro Phe Pro Lys Tyr Pro Pro Phe Thr Met Val
         65                  70                  75

AAC CCT AAC GTT CCA ACA AAC CCA TCT GGA GCT CAA GAG GAA TCA GAG     286
Asn Pro Asn Val Pro Thr Asn Pro Ser Gly Ala Gln Glu Glu Ser Glu
 80                  85                  90                  95

AAG CTA CCT TCT TCC CCA AGC AAA CTT AAC AAA GCT GGA CGA AAC GCA     334
Lys Leu Pro Ser Ser Pro Ser Lys Leu Asn Lys Ala Gly Arg Asn Ala
                100                 105                 110

TGAAAATTGT TGTTGGAAAC ATTTCTATGG TTTTACATTT TCATTAAAAT AAAATAAAAT   394

TGTATCTTTA ACAATTGAAT GGTAAGCG                                      422
```

( 2 ) INFORMATION FOR SEQ ID NO: 4:

( i ) SEQUENCE CHARACTERISTICS:

(A) LENGTH: 111 amino acids
(B) TYPE: amino acid
(D) TOPOLOGY: linear (ii) MOLECULE TYPE: protein (ix) FEATURE:
(D) OTHER INFORMATION: product="Bn E5 amino acid"

(xi) SEQUENCE DESCRIPTION: SEQ ID NO: 4:

```
Lys Val Ser Ser Phe Cys Leu Leu Leu Val Val Phe Phe Leu Asn
 1               5                  10                  15

Ser Gln Pro Ala Leu Ser Leu Arg Val Pro Lys Pro Gln Ser Glu Pro
            20              25                  30

Ala Ser Pro Gln Thr Met Ile Asp Asp Ser Ser Pro Met Gly Met Ile
        35                  40                  45

Asp His Ala Lys Ser Met Ile Ala Gly Phe Phe Ser His Lys Phe Pro
    50                  55                  60

Val Met Gly Trp Pro Phe Pro Lys Tyr Pro Pro Phe Thr Met Val Asn
65                  70                  75                  80

Pro Asn Val Pro Thr Asn Pro Ser Gly Ala Gln Glu Glu Ser Glu Lys
                85              90                  95

Leu Pro Ser Ser Pro Ser Lys Leu Asn Lys Ala Gly Arg Asn Ala
            100             105                 110
```

(2) INFORMATION FOR SEQ ID NO: 5:

(i) SEQUENCE CHARACTERISTICS:
(A) LENGTH: 398 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: CDS
(B) LOCATION: 1..315
(D) OTHER INFORMATION: /codon_start=1
/ product="Bn E3"

(xi) SEQUENCE DESCRIPTION: SEQ ID NO: 5:

```
GCC CTC CTC GTC GTC GTC TTC TTC CTC AGT TCT CAA CCT GCA CTC TCA     48
Ala Leu Leu Val Val Val Phe Phe Leu Ser Ser Gln Pro Ala Leu Ser
 1               5                  10                  15

CTC CGT CTC CCA AAA CCG CAG TCA GAA CTA GCA TCA CCT CAA ACC ATG     96
Leu Arg Leu Pro Lys Pro Gln Ser Glu Leu Ala Ser Pro Gln Thr Met
            20              25                  30

ATC GAT GAC TCA TCT CCA ATG GGA ATG ATC GAC CAT GCA AAA GCC ATG    144
Ile Asp Asp Ser Ser Pro Met Gly Met Ile Asp His Ala Lys Ala Met
        35                  40                  45

ATT GCT GGA TTC TTC AGC CAC AAG TTT CCA CTA ATG GGC TGG CCT TTC    192
Ile Ala Gly Phe Phe Ser His Lys Phe Pro Leu Met Gly Trp Pro Phe
    50                  55                  60

CCA AAG TAC CCA CCC TTC ACA ATG GTT AAC CCT AAC GTT CCA ACA AAA    240
Pro Lys Tyr Pro Pro Phe Thr Met Val Asn Pro Asn Val Pro Thr Lys
65                  70                  75                  80

CCA TCT GGA GCT CAA GAG GAA TCA GAG AAG TTA CCT TCT TCC CCA AGC    288
Pro Ser Gly Ala Gln Glu Glu Ser Glu Lys Leu Pro Ser Ser Pro Ser
                85              90                  95

AAA CTT AAC AAA GAT GGA CGA AAC GCA TGAAAATTGC TGTTGGAAAC          335
Lys Leu Asn Lys Asp Gly Arg Asn Ala
            100             105

ATTTCTATGG TTTTACATTT TCATTAAAAT AAAGAAATTG TATCTTTAAC AATTGAATGG  395
```

TAA                                                                                                          398

( 2 ) INFORMATION FOR SEQ ID NO: 6:

( i ) SEQUENCE CHARACTERISTICS:
        ( A ) LENGTH: 105 amino acids
        ( B ) TYPE: amino acid
        ( D ) TOPOLOGY: linear ( i i ) MOLECULE TYPE: protein ( i x ) FEATURE:
        ( D ) OTHER INFORMATION: product="Bn E3 amino acid"

( x i ) SEQUENCE DESCRIPTION: SEQ ID NO: 6:

```
Ala Leu Leu Val Val Val Phe Phe Leu Ser Ser Gln Pro Ala Leu Ser
 1               5                  10                  15
Leu Arg Leu Pro Lys Pro Gln Ser Glu Leu Ala Ser Pro Gln Thr Met
            20                  25                  30
Ile Asp Asp Ser Ser Pro Met Gly Met Ile Asp His Ala Lys Ala Met
        35                  40                  45
Ile Ala Gly Phe Phe Ser His Lys Phe Pro Leu Met Gly Trp Pro Phe
    50                  55                  60
Pro Lys Tyr Pro Pro Phe Thr Met Val Asn Pro Asn Val Pro Thr Lys
65                  70                  75                  80
Pro Ser Gly Ala Gln Glu Glu Ser Glu Lys Leu Pro Ser Ser Pro Ser
                85                  90                  95
Lys Leu Asn Lys Asp Gly Arg Asn Ala
            100                 105
```

( 2 ) INFORMATION FOR SEQ ID NO: 7:

( i ) SEQUENCE CHARACTERISTICS:
        ( A ) LENGTH: 1276 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 770..1126
        ( D ) OTHER INFORMATION: /codon_start=770
                / product="At A3 gene"

( x i ) SEQUENCE DESCRIPTION: SEQ ID NO: 7:

```
GTCGACACTA TTTGTTAATC AGTAGACTCA TTTGTGCTGC CTTTGGCTTC TTTTCGTCGG    60
AAAAACAGCT GAATGTGACT CTAATTTCGG CGGCAGCAAA CGCGGCGGCG TTCATGGCGG   120
AGGTAGGAAA GAACGGGAAC AAACACGCGA GATGGGACAA AATCTGTGAC AGATTCGCCA   180
CTTACTGTGA TCACGGCGCC GGAGCATTAA TCGCCGCATT CGCCGGCGTA ATCCTTATGC   240
TCATCATCTC CGCCGCGTCA ATCTCTCGTC TCGTCCAACC TAATAAATGC TGCTCCACCA   300
CCGCATCTCC CTCGGTCGTC CCCTGAAAAC ATACACACGT GTCACGTTCC CCTGTTATTT   360
TCCTTTTCTT TTCTTACTTC TTTGTTTCTT CTTGAGTGTG TGGTGTGTAT CTCGAGTGAA   420
TGTGATTGAT CAGATTGTGT AAGCATTTGG CTCGTCTCTT CTTTGTAAAA CTTTCTTCTT   480
ATGGTTTATT CTTAAACCAA TTCTCCGACT AGGGTTAGGT TACTAAAATA TCCATTACCT   540
ATACTCGTTA TCAATACCCA TACTCGTTAT ATCAACCATA AATCATCTCT CATAGTCATG   600
CTCAAATCAT GAACCTTTTT AATTCGAATA CTGGTTTAGG TAAGAAGTAG AATCCCAACG   660
```

```
TAAAAAACAC ATCTCTTCTA CAAACTCAAA AATCACTACT ATATAAGATT ACCAAGAAAC        720

CCCATAAAAC ACAATCACAA ACAAGAGCTC AAAAACACCA AAGCAAACA ATG TCG           775
                                                      Met Ser
                                                        1

AAA ATC TCA AAA GCT TCT TCT CTC TGT TTA CTC CTT CTC GTC TTC TTC         823
Lys Ile Ser Lys Ala Ser Ser Leu Cys Leu Leu Leu Leu Val Phe Phe
          5                  10                  15

CTC TTC AGT TCC CGA CCC GCA CTC TCA CTC CGT GGC CCA AAA CTT CAA         871
Leu Phe Ser Ser Arg Pro Ala Leu Ser Leu Arg Gly Pro Lys Leu Gln
         20                  25                  30

TCA TCG GAA CCA AAA TCA GCT CAA ACC CTA ATG GAT GAT TCG TCT TCA         919
Ser Ser Glu Pro Lys Ser Ala Gln Thr Leu Met Asp Asp Ser Ser Ser
 35                  40                  45                   50

ATG AAC AAG ATC AAC TCT GGA AAT GCA AAA ACC ATG ATT GCT GGT TTC         967
Met Asn Lys Ile Asn Ser Gly Asn Ala Lys Thr Met Ile Ala Gly Phe
                 55                  60                  65

TTC AGT CAC AAG TTT CCA TTA AAG GGC TGG CCT TTC CCT AAG TAC CCA        1015
Phe Ser His Lys Phe Pro Leu Lys Gly Trp Pro Phe Pro Lys Tyr Pro
             70                  75                  80

CCT TTC CCT ATG GTT AAC CCT AAT ATT GCA ACA AAC CCA TCT GGA GCT        1063
Pro Phe Pro Met Val Asn Pro Asn Ile Ala Thr Asn Pro Ser Gly Ala
         85                  90                  95

CAA GAG GAA TCC GCA AAG TTA CCT TCT TCT CCA AGC AAA GAC AAC AAA        1111
Gln Glu Glu Ser Ala Lys Leu Pro Ser Ser Pro Ser Lys Asp Asn Lys
    100                 105                 110

GAT GGA CGA AAC GCT TGAAGATTAG AGTTTACTTA TTTATATGGT TTTTACCATT        1166
Asp Gly Arg Asn Ala
115

GCATCAAATA AAAAATGTAC CTTAACAAT TAAATGGTAA AAGAAAAAG ATATTTATAT        1226

ATCATCAGCT CGAAGCGATT TTGTTATGAC AGTTACAGGA ATATTAACAA                 1276
```

(2) INFORMATION FOR SEQ ID NO: 8:

(i) SEQUENCE CHARACTERISTICS:
        (A) LENGTH: 119 amino acids
        (B) TYPE: amino acid
        (D) TOPOLOGY: linear (ii) MOLECULE TYPE: protein (ix) FEATURE:
        (D) OTHER INFORMATION: product="At A3 amino acid"

(xi) SEQUENCE DESCRIPTION: SEQ ID NO: 8:

```
Met Ser Lys Ile Ser Lys Ala Ser Ser Leu Cys Leu Leu Leu Val
 1               5                  10                  15

Phe Phe Leu Phe Ser Ser Arg Pro Ala Leu Ser Leu Arg Gly Pro Lys
             20                  25                  30

Leu Gln Ser Ser Glu Pro Lys Ser Ala Gln Thr Leu Met Asp Asp Ser
         35                  40                  45

Ser Ser Met Asn Lys Ile Asn Ser Gly Asn Ala Lys Thr Met Ile Ala
     50                  55                  60

Gly Phe Phe Ser His Lys Phe Pro Leu Lys Gly Trp Pro Phe Pro Lys
 65                  70                  75                  80

Tyr Pro Pro Phe Pro Met Val Asn Pro Asn Ile Ala Thr Asn Pro Ser
             85                  90                  95

Gly Ala Gln Glu Glu Ser Ala Lys Leu Pro Ser Ser Pro Ser Lys Asp
         100                 105                 110

Asn Lys Asp Gly Arg Asn Ala
         115
```

( 2 ) INFORMATION FOR SEQ ID NO: 9:

( i ) SEQUENCE CHARACTERISTICS:
         ( A ) LENGTH: 490 base pairs
         ( B ) TYPE: nucleic acid
         ( C ) STRANDEDNESS: double
         ( D ) TOPOLOGY: linear ( i i ) MOLECULE TYPE: DNA (genomic)

( i x ) FEATURE:
         ( A ) NAME/KEY: CDS
         ( B ) LOCATION: 9..296
         ( D ) OTHER INFORMATION: /codon_start=9
                              / product="Bn A9 gene"

( x i ) SEQUENCE DESCRIPTION: SEQ ID NO: 9:

```
TAAACAAA ATG GAA TTT CTC AAA TCC TTT ACA ACT ATT CTC TTT GTA ATG            50
         Met Glu Phe Leu Lys Ser Phe Thr Thr Ile Leu Phe Val Met
          1           5                  10

TTT CTG GCC ATG AGC GCT CTG GAG ACC GTA CCT ATG GTT CGA GCT CAA             98
Phe Leu Ala Met Ser Ala Leu Glu Thr Val Pro Met Val Arg Ala Gln
 15              20                  25                  30

CAA TGC CTA GAC AAT TTG AGC AAT ATG CAG GTG TGT GCG CCG CTG GTT            146
Gln Cys Leu Asp Asn Leu Ser Asn Met Gln Val Cys Ala Pro Leu Val
                 35                  40                  45

CTG CCT GGT GCA GTC AAT CCA GCC CCG AAT TCA AAT TGC TGC ATT GCT            194
Leu Pro Gly Ala Val Asn Pro Ala Pro Asn Ser Asn Cys Cys Ile Ala
             50                  55                  60

CTC CAA GCA ACT AAC AAA GAT TGT ATA TGT AAC GCC CTT CGA GCA GCC            242
Leu Gln Ala Thr Asn Lys Asp Cys Ile Cys Asn Ala Leu Arg Ala Ala
         65                  70                  75

ACC ACA TTT ACC ACT ACT TGC AAC CTC CCC TCT TTA GAT TGT GGT ATA            290
Thr Thr Phe Thr Thr Thr Cys Asn Leu Pro Ser Leu Asp Cys Gly Ile
     80                  85                  90

ACC ATA TGAGTGGTTT CAGCAACGGT CAGTTCCGAG GATTGGGGA GTTGGTCTG               346
Thr Ile
 95

CAAAAGACAA CAAGAATAAA AGTATTAAAA TAACGAGAAA GTGTGTGTGT TTTTTTTAA            406

TTTGGTCTGT TGTTCGGTTG GTTCAATACT TAAATATGAC CCATCAATTA ATATCGTTTT          466

CATATTTATT ATGGTAATAT TTTT                                                 490
```

( 2 ) INFORMATION FOR SEQ ID NO: 10:

( i ) SEQUENCE CHARACTERISTICS:
         ( A ) LENGTH: 96 amino acids
         ( B ) TYPE: amino acid
         ( D ) TOPOLOGY: linear ( i i ) MOLECULE TYPE: protein ( i x ) FEATURE:
         ( D ) OTHER INFORMATION: product="At A9 amino acid"

( x i ) SEQUENCE DESCRIPTION: SEQ ID NO: 10:

```
Met Glu Phe Leu Lys Ser Phe Thr Thr Ile Leu Phe Val Met Phe Leu
 1               5                  10                  15

Ala Met Ser Ala Leu Glu Thr Val Pro Met Val Arg Ala Gln Gln Cys
             20                  25                  30

Leu Asp Asn Leu Ser Asn Met Gln Val Cys Ala Pro Leu Val Leu Pro
             35                  40                  45

Gly Ala Val Asn Pro Ala Pro Asn Ser Asn Cys Cys Ile Ala Leu Gln
         50                  55                  60
```

Ala Thr Asn Lys Asp Cys Ile Cys Asn Ala Leu Arg Ala Ala Thr Thr
65                  70                  75                  80

Phe Thr Thr Thr Cys Asn Leu Pro Ser Leu Asp Cys Gly Ile Thr Ile
                85                  90                  95

(2) INFORMATION FOR SEQ ID NO: 11:

(i) SEQUENCE CHARACTERISTICS:
        (A) LENGTH: 1952 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1461..1781
        (D) OTHER INFORMATION: /codon_start=1461
        / product="At A9 gene"

(xi) SEQUENCE DESCRIPTION: SEQ ID NO: 11:

```
TCTAGACATA ACGGTGAGAG TTAATATTAA AATTTCAGGC GAGAAAAATG ATACTTGAAA      60
AATATTATGA TCGTTTTGGA TATTCCTTAC ATCGAGTGAA TGTTGGTTTG ATTCATCTTC     120
CAAGTGTTCT GCAAACGTAT ATTAAAGGTT TATTAACTGG TAAGAGATTA ACCGGGTTTT     180
GGTTCAGCAT ATACCATGAT TGACTAACTG ATCAAATAGT CTTTACTTAT TATATAAAGA     240
CGATACTATT GGTCATGCTA CAAAATCAAG TCATACCATA TCCTGAGAAT GAATGTGGAG     300
AATCGTTATA AGGCATAAGT GTGGGTATTG ATCGTGGTAC GAACAACCGC CTTGGCATCA     360
ACATTAGCCA CGATATCCAA CATTTGAAGC ATTGCCTATG GCGAGTGTTT GGTTGGTTTT     420
GAAACTGATG ATGATAACCA GAACGAGAAA TGTCTTGTGA AGTATAATGT TCCGATGAAT     480
TGGGATTATA ATAATGTGTA GACATTGTAG GTTGGTTTTG ATGATGATAA GTAATCATTG     540
GAGAATTGTC TAACACATGC ACTGGAGAAT TATTGACTCT ACCACGTTCT CTTTGATATT     600
CCTCGATTTT CCTCGTGATT TCATCAGCCT CTCCGAAAAA GTAATTGTAT CCACTAGAAC     660
TTTGGGAATC TCCCATCTAA TTTATGTATT AGAGAAGTTA TAATATTTTG GGGAAATAGA     720
TTTTCTCTAC TGATTTTGTT GTGTGACATT ATATTTTTAT AAGTACATGT TTCTGTTTCG     780
TTATATTGTT GTCGTGGTTG AGTCTTTATT AGAGCATGTA AATATGTTTA TGAAATAAGC     840
GAGAAAGGAA TTAATTAAAC GTATCGAGTG ATAAATGCTT TAATGGATTC GAGATTTAGT     900
ATTCTTAAAT TTTTGTTTCA TTATCATTGA TTATAAAACT AAGTTATGTT GATCTCAAAT     960
CCTTAATTAT GTTCTCCTAA GAAGAGTACA AGTGGTGGGA ACGAAGATG AGTAAAATAC    1020
TAAAAATCTT TTCTCAAAAG TCAAATCGCA TTAGTTAACA AAAACAAACC ATGTGTTACC    1080
GTCAAATCAA TGTGTTTAAA AGATGTTAAC CACTAATCAA GCATTACGT GTAACCGGAT    1140
CAACCGGATT TGGGTTTTGA ATATGTTGTG GAGATGTATA TAAATGATAA ATTAATTGAA    1200
TATCTTAATT AATCTGTGAA AGAAACTACA TCACACACTT TGTTATTCC CCTAGCTTTT    1260
AGTTTTTTTA TCATGCAAAA CTTATGAAGT AACTAGATCA AGATCACAAA AAAAAAGCAT    1320
CACTTCACTT CATGACCTAA TTATTCTCGA AGCCCAAAAC TATTTACATA CACTTTTATT    1380
CTATAAATAT AGATGATGGA ATTCACCAAT CCAAAAGTGA ATAAAAAACA CAAGTACAAA    1440
CAATATAGTA TCTAATTAGA ATG GTA TCT CTA AAG TCC CTT GCT GCT ATT       1490
               Met Val Ser Leu Lys Ser Leu Ala Ala Ile
               1             5                       10

CTC GTT GCC ATG TTT CTT GCC ACC GGA CCT ACG GTT CTA GCC CAG CAG      1538
Leu Val Ala Met Phe Leu Ala Thr Gly Pro Thr Val Leu Ala Gln Gln
```

|  |  |  |  |  |  |  |  |  |  |  |  |  |  |  |  |
|---|---|---|---|---|---|---|---|---|---|---|---|---|---|---|---|
| TGC | AGA | GAC | GAA | CTG | AGC | AAT | GTG | CAG | GTG | TGC | GCG | CCG | CTG | CTT | CTG |
| Cys | Arg | Asp | Glu | Leu | Ser | Asn | Val | Gln | Val | Cys | Ala | Pro | Leu | Leu | Leu |
|  |  |  | 30 |  |  |  |  | 35 |  |  |  |  | 40 |  |  |

1586

|  |  |  |  |  |  |  |  |  |  |  |  |  |  |  |  |
|---|---|---|---|---|---|---|---|---|---|---|---|---|---|---|---|
| CCC | GGT | GCG | GTC | AAT | CCT | GCC | GCG | AAC | TCA | AAT | TGC | TGC | GCT | GCC | CTC |
| Pro | Gly | Ala | Val | Asn | Pro | Ala | Ala | Asn | Ser | Asn | Cys | Cys | Ala | Ala | Leu |
|  |  | 45 |  |  |  |  | 50 |  |  |  |  | 55 |  |  |  |

1634

|  |  |  |  |  |  |  |  |  |  |  |  |  |  |  |  |
|---|---|---|---|---|---|---|---|---|---|---|---|---|---|---|---|
| CAA | GCA | ACT | AAC | AAA | GAT | TGT | CTA | TGT | AAC | CGT | CTT | CGA | GCA | GCC | ACC |
| Gln | Ala | Thr | Asn | Lys | Asp | Cys | Leu | Cys | Asn | Arg | Leu | Arg | Ala | Ala | Thr |
|  | 60 |  |  |  |  | 65 |  |  |  |  | 70 |  |  |  |  |

1682

|  |  |  |  |  |  |  |  |  |  |  |  |  |  |  |  |
|---|---|---|---|---|---|---|---|---|---|---|---|---|---|---|---|
| ACA | CTT | ACC | TCT | CTT | TGT | AAC | CTC | CCC | TCT | TTT | GAT | TGT | GGT | AAG | ATG |
| Thr | Leu | Thr | Ser | Leu | Cys | Asn | Leu | Pro | Ser | Phe | Asp | Cys | Gly | Lys | Met |
| 75 |  |  |  |  | 80 |  |  |  |  | 85 |  |  |  |  | 90 |

1730

|  |  |  |  |  |  |  |  |  |  |  |  |  |  |  |  |
|---|---|---|---|---|---|---|---|---|---|---|---|---|---|---|---|
| ATC | CAT | CGA | TTA | AAA | CCT | TTT | TTA | CTA | GAT | TTT | TAT | AAA | TTA | TTC | CAT |
| Ile | His | Arg | Leu | Lys | Pro | Phe | Leu | Leu | Asp | Phe | Tyr | Lys | Leu | Phe | His |
|  |  |  |  | 95 |  |  |  |  | 100 |  |  |  |  | 105 |  |

1778

|  |  |  |  |  |  |
|---|---|---|---|---|---|
| CAA | TAGTGTTTGT | TTTATATTTG | TTCTCATGAT | TTTTGGACT | TATGTTTGT |
| Gln |  |  |  |  |  |

1831

GAACTGTGCA GGCATAAGTG CCTAGTTGAA CAACATTCAG TTCCGAGGAT TGGGGAGTT 1891

TGGTCTGCAA ACGACAAGAC GAATAAAATA AAATAATGAG AAATACACTA TTTAGTGTTT 1951

T 1952

( 2 ) INFORMATION FOR SEQ ID NO: 12:

( i ) SEQUENCE CHARACTERISTICS:
        ( A ) LENGTH: 107 amino acids
        ( B ) TYPE: amino acid
        ( D ) TOPOLOGY: linear ( i i ) MOLECULE TYPE: protein ( i x ) FEATURE:
        ( D ) OTHER INFORMATION: product="At A9 amino acid"

( x i ) SEQUENCE DESCRIPTION: SEQ ID NO: 12:

| Met | Val | Ser | Leu | Lys | Ser | Leu | Ala | Ala | Ile | Leu | Val | Ala | Met | Phe | Leu |
|---|---|---|---|---|---|---|---|---|---|---|---|---|---|---|---|
| 1 |  |  |  | 5 |  |  |  |  | 10 |  |  |  |  | 15 |  |

| Ala | Thr | Gly | Pro | Thr | Val | Leu | Ala | Gln | Gln | Cys | Arg | Asp | Glu | Leu | Ser |
|---|---|---|---|---|---|---|---|---|---|---|---|---|---|---|---|
|  |  |  | 20 |  |  |  |  | 25 |  |  |  |  | 30 |  |  |

| Asn | Val | Gln | Val | Cys | Ala | Pro | Leu | Leu | Leu | Pro | Gly | Ala | Val | Asn | Pro |
|---|---|---|---|---|---|---|---|---|---|---|---|---|---|---|---|
|  |  | 35 |  |  |  |  | 40 |  |  |  |  | 45 |  |  |  |

| Ala | Ala | Asn | Ser | Asn | Cys | Cys | Ala | Ala | Leu | Gln | Ala | Thr | Asn | Lys | Asp |
|---|---|---|---|---|---|---|---|---|---|---|---|---|---|---|---|
|  | 50 |  |  |  |  | 55 |  |  |  |  | 60 |  |  |  |  |

| Cys | Leu | Cys | Asn | Arg | Leu | Arg | Ala | Ala | Thr | Thr | Leu | Thr | Ser | Leu | Cys |
|---|---|---|---|---|---|---|---|---|---|---|---|---|---|---|---|
| 65 |  |  |  |  | 70 |  |  |  |  | 75 |  |  |  |  | 80 |

| Asn | Leu | Pro | Ser | Phe | Asp | Cys | Gly | Lys | Met | Ile | His | Arg | Leu | Lys | Pro |
|---|---|---|---|---|---|---|---|---|---|---|---|---|---|---|---|
|  |  |  |  | 85 |  |  |  |  | 90 |  |  |  |  | 95 |  |

| Phe | Leu | Leu | Asp | Phe | Tyr | Lys | Leu | Phe | His | Gln |
|---|---|---|---|---|---|---|---|---|---|---|
|  |  |  | 100 |  |  |  |  | 105 |  |  |

( 2 ) INFORMATION FOR SEQ ID NO: 13:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 13:

```
GGGTCTAGAC CATGGCACAG GTTATCAACA CGTTTGACGG                    40
```

( 2 ) INFORMATION FOR SEQ ID NO: 14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 14:

```
GTAAAACGAC GGCCAGTGCC                                          20
```

( 2 ) INFORMATION FOR SEQ ID NO: 15:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 15:

```
GGGTCTAGAC CATGGTAATT AGATACTATA TTGTTTGTAC                    40
```

( 2 ) INFORMATION FOR SEQ ID NO: 16:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 16:

```
AATACGACTC ACTATAGG                                            18
```

( 2 ) INFORMATION FOR SEQ ID NO: 17:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 17:

```
CGCTCTAGAC CATGGCTGCT ATCACACTCC TAGG                          34
```

( 2 ) INFORMATION FOR SEQ ID NO: 18:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 18:

```
GGGCCGCGGT CACCCAAAGT TGATATTATA TTTGGGC                       37
```

We claim:

1. Isolated DNA comprising a promoter having tapetum-specific activity which naturally drives the expression of a gene encoding a 12.9 kDa tapetum-specific protein as shown in FIG. 4 (SEQ ID No. 7) in *Arabidopsis thaliana*.

2. Isolated DNA comprising a promoter having tapetum-specific activity which naturally drives the expression of a gene encoding an 11.6 kDa tapetum-specific protein as shown in FIG. 7 (SEQ ID No. 11) in *Arabidopsis thaliana*.

3. Isolated DNA comprising a promoter having tapetum-specific activity which naturally drives the expression of a gene encoding a 10.3 kDa tapetum-specific protein in *Brassica napus*, said gene hybridizing under stringent conditions to the cDNA of FIG. 5 (SEQ ID No. 9).

4. Isolated DNA comprising a promoter having tapetum-specific activity in *Brassicaceae* which is sufficient in size to naturally drive the expression of a gene encoding a tapetum-specific protein, said gene hybridizing under stringent conditions to the gene of FIG. 4 (SEQ ID No. 7).

5. Isolated DNA comprising a promoter having tapetum-specific activity in *Brassicaceae* which is sufficient in size to naturally drive the expression of a gene encoding a tapetum-specific protein, said gene hybridizing under stringent conditions to the cDNA of FIG. 1 (SEQ ID No. 1).

6. Isolated DNA comprising a promoter having tapetum-specific activity in *Brassicaceae* which is sufficient in size to naturally drive the expression of a gene encoding a tapetum-specific protein, wherein said gene hybridizing under stringent conditions to the gene of FIG. 7 (SEQ ID No. 11).

7. Isolated DNA comprising a promoter having tapetum-specific activity in *Brassicaceae* which is sufficient in size to naturally drive the expression of a gene encoding a tapetum-specific protein, wherein said gene hybridizing under stringent conditions to the cDNA of FIG. 8 (SEQ ID No. 9).

8. DNA as claimed in any one of claims 1 to 7, wherein said promoter having tapetum-specific activity is operatively linked to DNA which, when expressed, causes male sterility in a plant.

9. The DNA as claimed in claim 8, wherein the male sterility effecting DNA encodes a lytic enzyme.

10. The DNA as claimed in claim 9, wherein the lytic enzyme causes lysis of nucleic acid, protein, carbohydrate or lipid.

11. The DNA as claimed in claim 10, wherein the lytic enzyme is a ribonuclease or a deoxyribonuclease.

12. The DNA as claimed in claim 11, wherein the lytic enzyme is barnase.

13. The DNA as claimed in claim 10, wherein the lytic enzyme of carbohydrate is glucanase.

14. The DNA as claimed in claim 13, comprising a signal sequence in a translational fusion with the glucanase coding sequence.

15. The DNA as claimed in claim 10, wherein the proteolytic enzyme is actinidin or papain.

16. The DNA as claimed in claim 8, wherein the male sterility effecting DNA encodes an enzyme catalyzing the synthesis of a phytohormone, wherein said enzyme is isopentyl transferase.

17. DNA as claimed in any one of claims 1 to 7, further comprising a 3' transcription regulation sequence.

18. The DNA as claimed in claim 17, wherein the 3' transcription regulation sequence is derived from the Cauliflower Mosaic Virus 35S gene.

19. The DNA as claimed in claims 8, which is in the form of a recombinant vector.

20. The DNA as claimed in claim 19, wherein the recombinant vector is a cloning vector and comprises one or more selectable markers.

21. A microbial host cell transfected or transformed with a vector as claimed in claim 19.

22. A microbial host cell transfected or transformed, with a vector as claimed in claim 20.

23. DNA as claimed in any one of claims 1 to 7, comprising a marker sequence which enables a plant transformed with said DNA to be distinguished from plants not so transformed.

24. The DNA as claimed in claim 23, wherein said marker sequence confers antibiotic or herbicide resistance or codes for glucuronidase.

25. The DNA as claimed in claim 24, wherein said marker sequence is under the control of a second promoter which does not have tapetum-specific activity.

26. The DNA as claim in claim 25, wherein said second promoter is derived from the Cauliflower Mosaic Virus (CaMV) 35S gene.

27. A plant cell transformed with the DNA as claimed in any one of claims 1 to 7.

28. A plant, a part of a plant, or propagating material from a plant, each comprising plant cells transformed as claimed in claim 27.

* * * * *